United States Patent
Becker et al.

(10) Patent No.: US 10,964,407 B2
(45) Date of Patent: Mar. 30, 2021

(54) METHOD FOR ESTIMATING THE PROBE-TARGET AFFINITY OF A DNA CHIP AND METHOD FOR MANUFACTURING A DNA CHIP

(71) Applicants: BIOMERIEUX, Marcy l'Etoile (FR); HOSPICES CIVILS DE LYON, Lyons (FR)

(72) Inventors: Jérémy Becker, Chartres (FR); Philippe Perot, Saint-Yrieix (FR); François Mallet, Villeurbanne (FR)

(73) Assignees: BIOMERIEUX, Marcy l'Etoile (FR); HOSPICES CIVILS DE LYON, Lyons (FR)

( * ) Notice: Subject to any disclaimer, the term of this patent is extended or adjusted under 35 U.S.C. 154(b) by 899 days.

(21) Appl. No.: 15/532,220

(22) PCT Filed: Nov. 30, 2015

(86) PCT No.: PCT/FR2015/053256
§ 371 (c)(1),
(2) Date: Jun. 1, 2017

(87) PCT Pub. No.: WO2016/087756
PCT Pub. Date: Jun. 9, 2016

(65) Prior Publication Data
US 2017/0270242 A1    Sep. 21, 2017

(30) Foreign Application Priority Data
Dec. 1, 2014  (FR) .................................... 14 61722

(51) Int. Cl.
*G16B 25/00*  (2019.01)
*G16B 25/20*  (2019.01)

(52) U.S. Cl.
CPC .............. *G16B 25/00* (2019.02); *G16B 25/20* (2019.02)

(58) Field of Classification Search
None
See application file for complete search history.

(56) References Cited

U.S. PATENT DOCUMENTS

| | | |
|---|---|---|
| 2005/0026176 A1 | 2/2005 | Yoshii et al. |
| 2005/0250115 A1 | 11/2005 | Cherepinsky et al. |
| 2013/0338015 A1 | 12/2013 | Frezza et al. |

FOREIGN PATENT DOCUMENTS

CN   102959092 A   3/2013

OTHER PUBLICATIONS

Ono, Naoaki et al., "An improved physico-chemical model of hybridization on high-destiny oligonucleotide microarrays," Bioinformatics, pp. 1278-1285, 2008, No. 10, vol. 24.

Irizarry, Rafael A. et al., "Exploration, normalization, and summaries of high density oligonucleotide array probe level data," Biostatistics, 2003, pp. 249-264, vol. 4, No. 2.

"Design and Performace of the GeneChip Human Genome U133 Plus 2.0 and Human Genome U133A 2.0 Arrays," Affymetrix, pp. 1-9, Year =2003.

Gimenez, Juliette et al., "Custom human endogenous retroviruses dedicated microarry identifies self-induced HERV-W family elements reactivated in testicular cancer upon methylation control," Nucleic Acids Research, 2009, pp. 1-27.

Li, Chang et al., "Model-based analysis of oligonucleotide arrays: Expression index computation and outlier detection," Proceedings of the National Academmy of Science, 2001, pp. 31-36. vol. 98, No. 1.

Li, Heng et al., "Fast and accurate long-read alignment with Burrows-Wheeler transform," Bioinformatics, 2010, pp. 589-595, vol. 26, No. 5.

Zhang, Li et al., "A model of molecular interactions on short oligonucleotide microarrays," Nature biotechnology, 2003, pp. 818-821, vol. 21, No. 7.

"The MicroArray Quality Control (MAQC) project shows inter- and intraplatform reproducibility of gene expression measurements," Nature Biotechnology, 2006, pp. 1151-1161, vol. 24, No. 9.

Perot, Philippe et al., "Microarray-Based Sketches of the HERV Transcriptome Landscape," PLOS One, 2012, pp. 1-16, vol. 7, No. 6.

Tusher, Virginia Goss et al., "Significance analysis of microarrays applied to the ionizing radiation response," Proceedings of the National Academy of Sciences of the USA, 2001, pp. 5116-5121, vol. 98, No. 9.

(Continued)

*Primary Examiner* — G Steven Vanni
(74) *Attorney, Agent, or Firm* — Oliff PLC

(57) ABSTRACT

A method for estimating the affinity φ of a first DNA strand, or "probe", to be hybridized with a second DNA strand, or "target", to form a hybrid of length $L_{bp}$, the method comprising: in each division of a set of M divisions of the hybrid, counting the number of times in which each hybrid of a set of P DNA strand hybrids is present in the division, the hybrids being of length k less than the length $L_{bp}$, or "k-hybrids"; for each combination of mismatches of a set of L combinations of mismatches in a hybrid of length Lbp, determining whether the pair of mismatches is present in the hybrid; and calculating the affinity φ according to the relation:

$$\phi = \sum_{m=1}^{M} \sum_{p=1}^{P} x_{m,p} \cdot \hat{\beta}_{m,p} + \alpha.$$

13 Claims, 13 Drawing Sheets

(56) References Cited

OTHER PUBLICATIONS

Mie, Rui et al., "Probe selection for high-density oligonucleotide arrays," Proceedings of the National Academy of Science, 2003, pp. 11237-11242, vol. 100, No. 20.
Feb. 1, 2016 International Search Report issued in International Patent Application No. PCT/FR2015/053256.

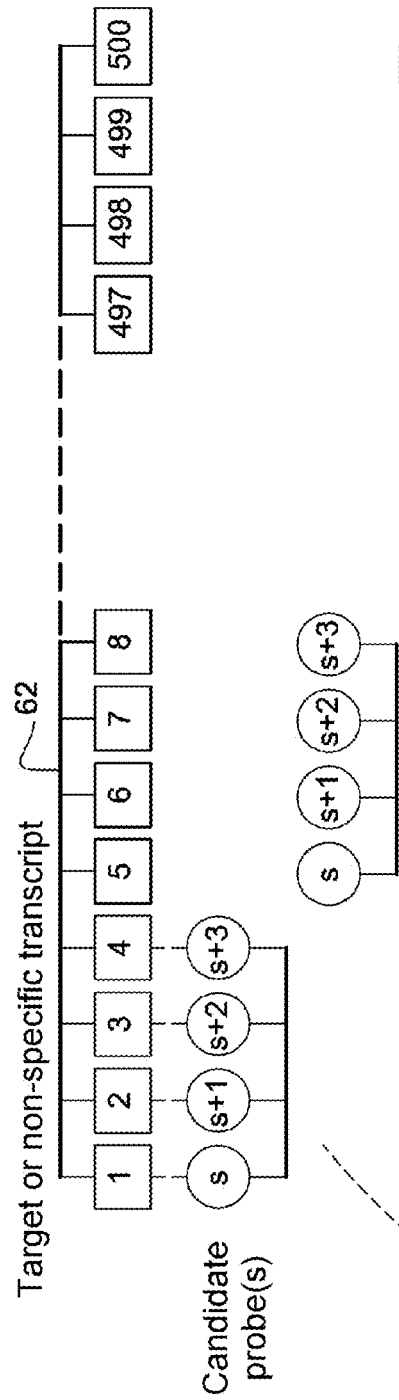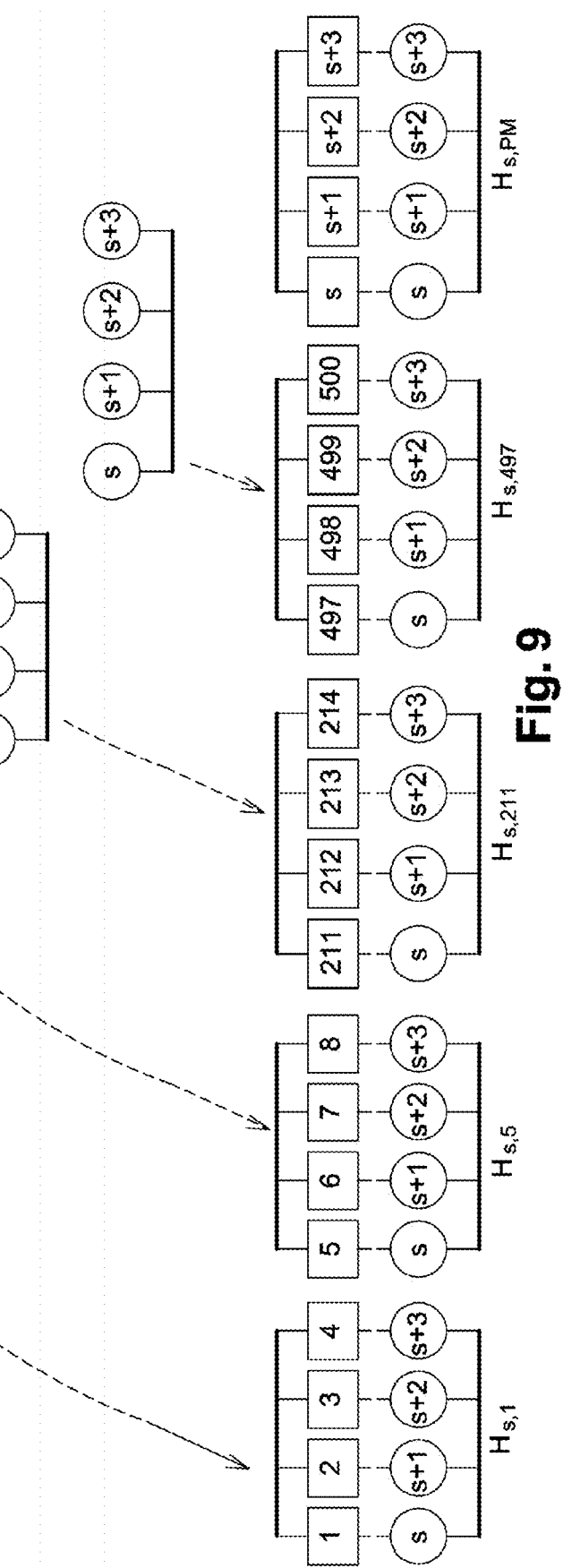
Fig. 8
Fig. 9

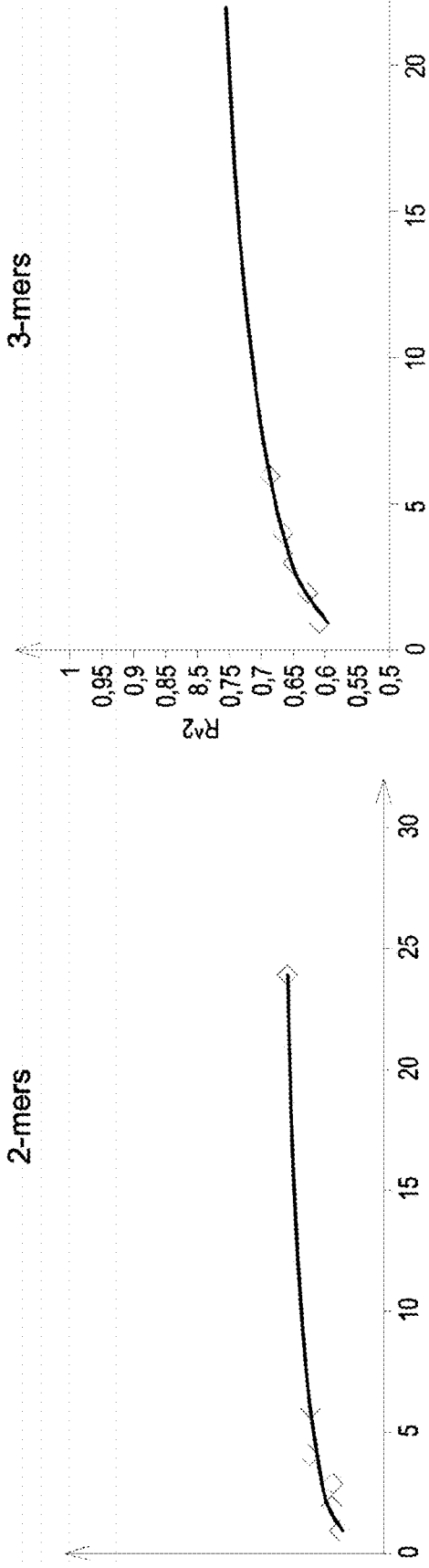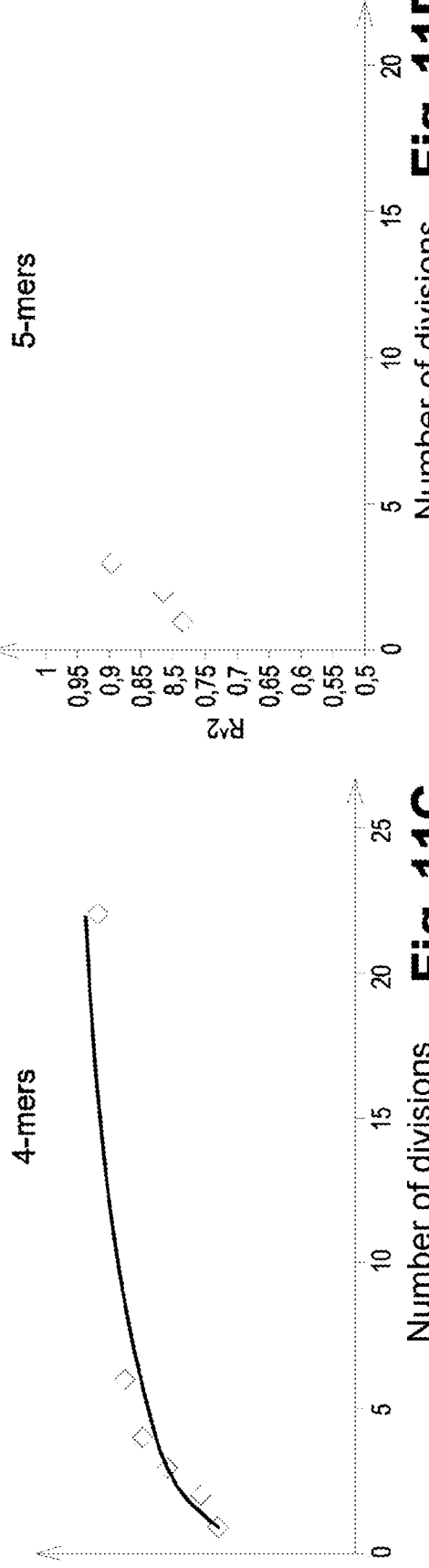
Fig. 11A  Fig. 11B  Fig. 11C  Fig. 11D

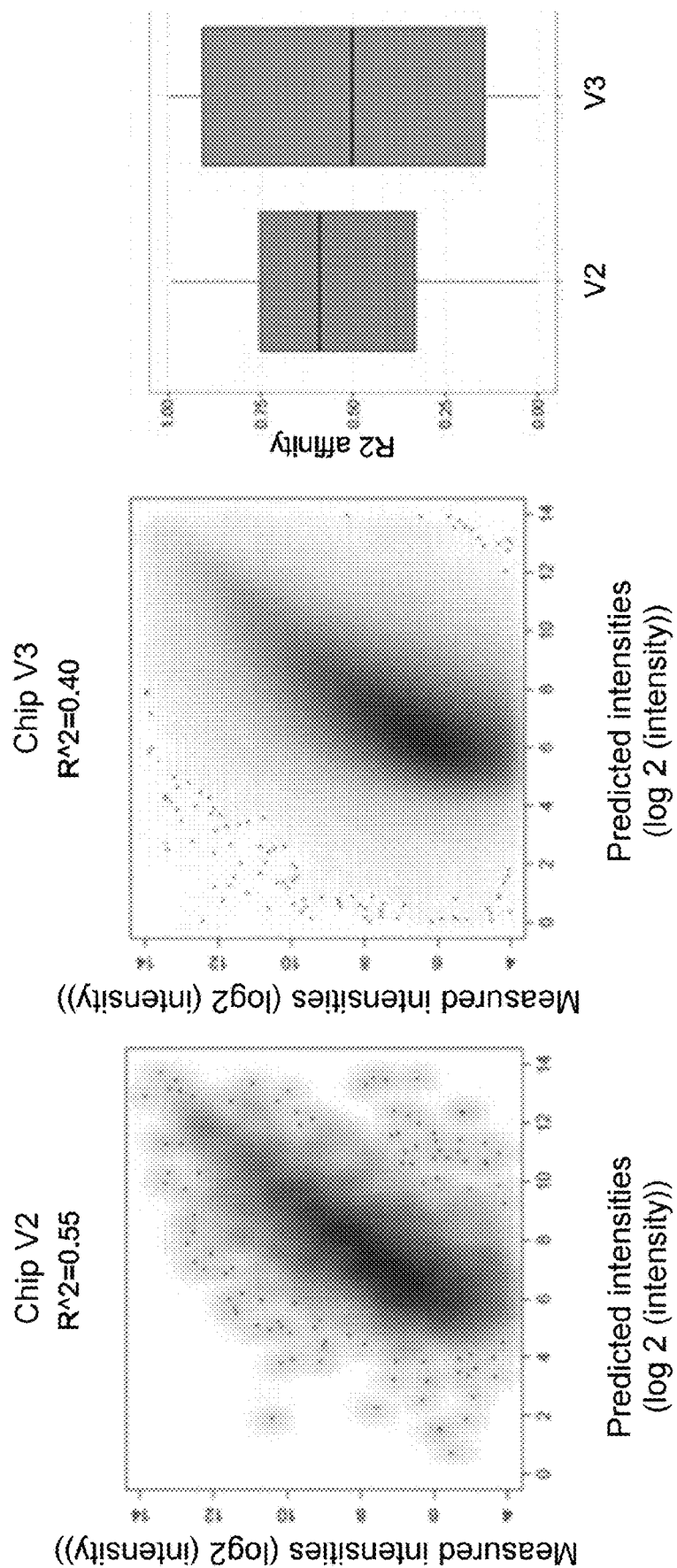

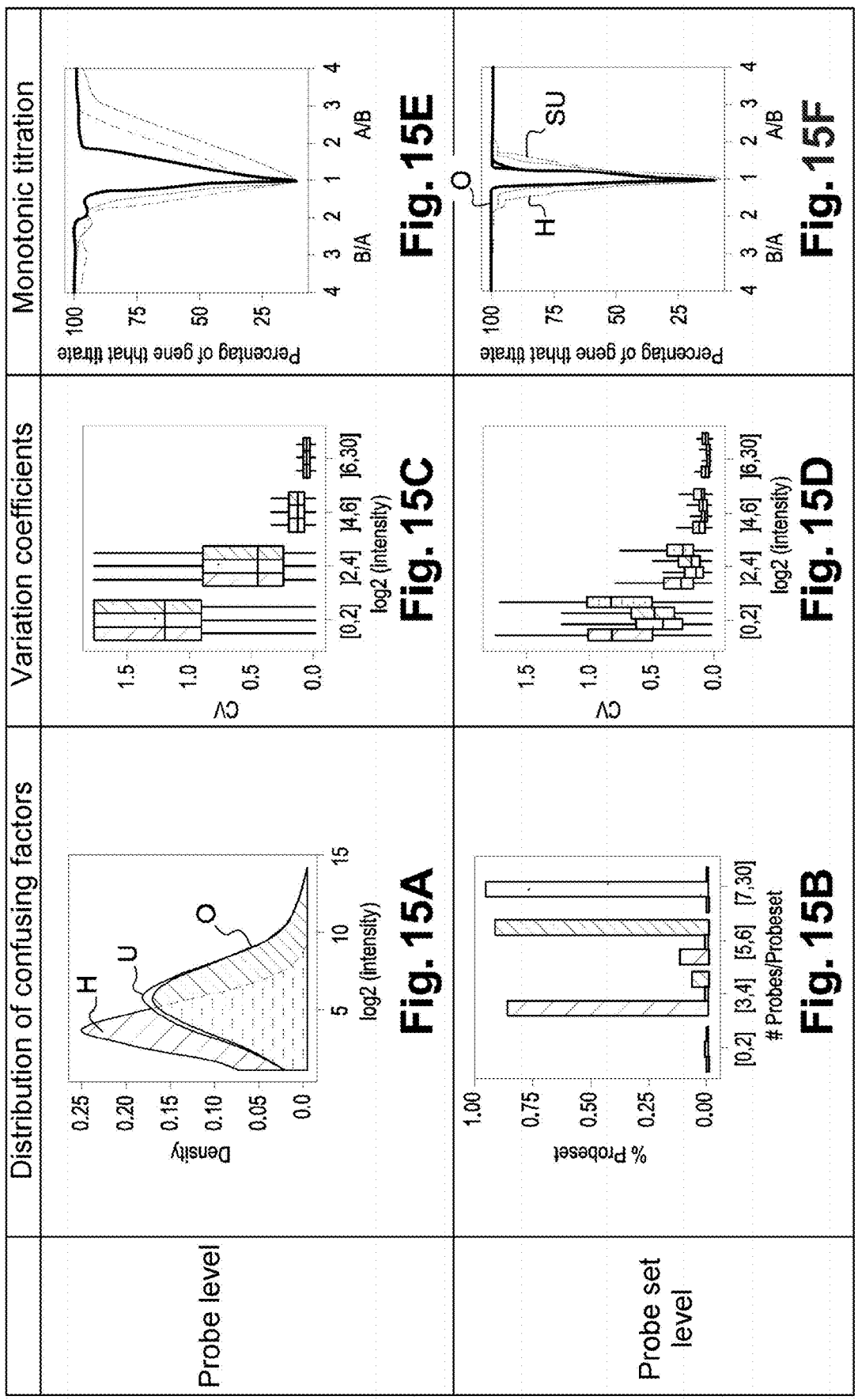

METHOD FOR ESTIMATING THE PROBE-TARGET AFFINITY OF A DNA CHIP AND METHOD FOR MANUFACTURING A DNA CHIP

The invention deals with the field of transcriptomes, notably the study of hybridization between DNA strands.

The invention is particularly applicable in the field of the design of hybridization supports, notably DNA chips.

STATE OF THE ART

A DNA chip measures the level of expression of transcripts based on the property of a simple DNA strand of spontaneously reforming a double strand when it is brought together with a complementary DNA strand, that is to say its property of hybridizing with a complementary strand. To know the level of expression of a transcript in a biological sample, a DNA chip comprises sequences of nitrogenous bases, called "probes" designed to be hybridized specifically with a set of transcripts of interest, or "target" transcripts. To improve the robustness of the measurement, a transcript is targeted by several probes, together forming a "probe set". For the purposes of high speed screening, a DNA chip thus comprises I "probe sets" targeting I transcripts, for a total of J different probes. For measurement purposes, each probe is repeated identically a large number of times, the repeated probes being arranged in a well.

The target transcript whose expression is sought, which can run to several thousands or tens of thousands of nitrogenous bases A, G, C, T, is first of all transformed, via an amplification process into a solution comprising smaller DNA fragments, of a length usually between 25 and 200 nitrogenous bases marked by a fluorescent colorant. The solution thus obtained is then deposited in the wells of the DNA chip. With each well corresponding to a probe, repeated several times and designed for a transcript, this therefore leads to the hybridization of some of these fragments with the probes of the well. After a washing of the DNA chip in order to keep only the hybrids formed in the wells, a measurement of the fluorescence in each well is then implemented by a high-resolution scanner, a measurement that is representative of the quantity of hybrids present in the well. The expressions "probe fluorescence" or "probe intensity" then apply.

To have a good understanding of the following, the following definitions have to be introduced. The term "probe" therefore refers to a sequence of nitrogenous bases, or "nucleotides", that make up a DNA chip, and more generally to any device using hybridization with probes. The term "target" refers to a sequence of nitrogenous bases, derived from a transcript, capable of forming, with its probe, a hybrid. The expression "specific target" relates to a target which corresponds to the portion of transcript identified, both in terms of base sequence and of positioning in the transcript, for which the probe has been designed. The term "perfect" or "identical" hybrid relates to a hybrid formed by a probe and a target which are strictly complementary to one another in terms of nitrogenous bases (hybrid better known as "perfect match"). The expression "mismatch" relates to a hybrid of a probe and of a target in which a base of the probe and a base of the target, one facing the other, are not complementary (better known as "mismatch") or to a base of the target or of the probe which is not facing any base (better known as "gap"). This is also referred to as a probe and a target being mismatched. The term "k-mer" relates to a sequence of k nucleic bases. The "length" of a nitrogenous base sequence corresponds to the number of nitrogenous bases that it contains. The length of a probe/target hybrid corresponds more generally to the length of the probe.

While the general principle of a DNA chip seems on the face of it to be simple, since it consists in choosing a probe which corresponds to a DNA sequence complementing a fragment of the transcript, putting it into practice to obtain quality DNA chips is however difficult.

In fact, first of all, it may be thought that it is sufficient to simply choose a probe which forms a perfect hybrid with a target. Now, a perfect hybrid may be too unstable to withstand the washing, which leads in the end to a measured signal that is too weak to determine the level of expression of the transcript. Note, thus, that, for a given transcript, the portions thereof giving rise to the probes are not equivalent, and that it is therefore best to choose the portions of transcript resulting in the obtention of probe/target hybrids that are sufficiently stable to obtain a meaningful measurement. Furthermore, a probe and a target, potentially exhibiting one or more mismatches, may also be hybridized stably. Such a target, being able to be different from the specific target, may originate from another transcript present in the biological sample, in which case a false detection or "false positive" is obtained.

This is why a probe is sought which, both:

targets only a single determined portion of the transcript, a portion which is unique, and which is not therefore found identically in the transcript itself in another position or in another transcript likely to be present in the biological sample, and exhibits a low affinity with any other target exhibiting a mismatch. The expression "specific probe" then applies; and exhibits a strong affinity with the specific target, that is to say forms a stable hybrid therewith. This is called a "strong affinity of the probe with the specific target", or "affine" or "sensitive" probe.

Bearing in mind that a transcript may comprise tens of thousands of bases, and that a biological sample may comprise many transcripts, without it being easily and efficiently possible to check the composition of the sample, it is easy to understand the number of probes, of a length less than a hundred or so bases, that would have to be designed and tested to retain only the specific and affine probes. Since the experimental design of a DNA chip is therefore difficult, even impossible, biocomputing tools have therefore been designed to assess the specificity and the affinity of the probes and thus assist in the design of a DNA chip.

For example, the document by Mei et al ("*Probe selection for high-density oligonucleotide arrays*", Proceedings of the National Academy of Science, 100(20):11237-11242, September 2003) describes a score quantifying the quality of a probe. This score comprises the product of a first term, quantifying the specificity of the probe, by a second term derived from the affinity of the probe. The first term determines the risk of cross-reactions between the probe and other transcripts, different from the target transcript, over the whole of the human genome. The second term, for its part, comprises a sensitivity term, expressed as the directing coefficient of the straight line $I=K+S \cdot \ln([T])$, in which I is the intensity of a given probe, S the sensitivity, K the target-probe affinity and [T] the target concentration. The authors show that this sensitivity term can be calculated using a hybridization model based on the nucleic sequence of the probes. According to this model, the probe is therefore considered, from the affinity point of view, only as a juxtaposition of bases with no particular link between them, nor any link with a target with which it can be hybridized.

This affinity model, sometimes called "any-position monomer model", is therefore expressed only as a function of the presence/absence of each base in each position.

This affinity model does however prove unsatisfactory because it does not take account of mismatches between a probe and a target, and seeks only to model the affinity of a probe with its specific target. More complex affinity models have therefore been designed to take account of the non-specific hybridizations, or cross-reactions. For example, the document by Zhang et al ("*A model of molecular interactions on short oligonucleotide microarrays*", Nature biotechnology, 21(7):818-821, July 2003) describes a statistical model expressing the measured intensity as the sum of two terms linked respectively to the hybridization of the probe with its specific target and the hybridization of the probe with the set of non-specific targets. In this document, the intensity of the $i^{th}$ well of the DNA chip, that is to say of the $i^{th}$ probe, reflecting the level of expression of the $j^{th}$ transcript, is thus predicted according to the relations:

$$\hat{I}_{ij} = \frac{N_j}{(1+e^{E_{ij}})} + \frac{N_j^*}{(1+e^{E_{ij}^*})} + B$$

$$E_{ij} = \sum_k \omega_k \cdot \varepsilon(b_k, b_{k+1})$$

$$E_{ij}^* = \sum_k \omega_k^* \cdot \varepsilon^*(b_k, b_{k+1})$$

in which:
$\hat{I}_{ij}$ is the predicted intensity;
$N_1$ is the quantity of targets, derived from the $j^{th}$ transcript, measured by the $j^{th}$ probe sets, present in the solution deposited on the DNA chip;
$\hat{N}_j^*$ is the quantity of targets, derived from different transcripts of the $j^{th}$ transcript targeted by the probes of the probe set, present in the solution deposited on the DNA chip;
$\varepsilon(b_k, b_{k+1})$ is the release energy of the pair $(b_k, b_{k+1})$ of consecutive cases of the probe, or "dimers", present respectively at the position k and k+1 in the probe, independently of the position of said pair in the probe, release energy of the pair when the probe is hybridized with its specific target, and therefore forms with this target a perfect hybrid;
$\omega_k$ is a factor quantifying the influence of the position of the pair $(b_k, b_{k+1})$ in the probe when the probe is hybridized with this target;
$\varepsilon^*(b_k, b_{k+1})$ is a release energy of the pair $(b_k, b_{k+1})$, independently of the position thereof in the probe, release energy of the pair when the probe is hybridized with a target derived from another transcript, and therefore that can include a mismatch; and
$\omega_k^*$ is a factor quantifying the influence of the position of the pair $(b_k, b_{k+1})$ in the probe when the latter is hybridized with this target; and
B is a scalar.

The value of these parameters is determined by implementing an identification on the basis of intensities measured by the authors of the document.

The first term $$\frac{N_j}{(1+e^{E_{ij}})},$$

corresponding to the contribution of the specific target, is equal to the quotient of the quantity of specific fragments hybridized on the DNA chip and of a term reflecting the affinity between the probe and its specific target, namely an exponential term with the energy needed to separate the probe and its specific target.

According to the model, the energy is equal to the sum of the respective contributions of the dimers $(b_k, b_{k+1})$ weighted by terms dependent on the position of the dimers. By definition, this term therefore stems exclusively from perfect hybrids formed in the probe set. For each dimer, there is therefore only a single configuration, namely the link to its complement.

The second term $$\frac{N_j^*}{(1+e^{E_{ij}^*})},$$

for its part, corresponds to the proportion of the non-specific probes. Now, unlike a probe hybridized with its specific target, when considering hybridization with targets of other transcripts, that is to say the cross-hybridizations, there may indeed be a perfect hybridization (if another transcript gives rise to a target identical to the specific target) but there is above all a hybridization with one or more mismatches. Thus, for a given dimer, there are no less than 24 different hybridization configurations. The second term therefore in no way differentiates the different types of mismatches.

This type of model poses a certain number of problems. First of all, a problem of identification arises. Note in fact that terms which are products of one another have to be identified. Without positing a certain number of additional constraints, not described in the document by Zhang, it is not therefore possible to know how an identification algorithm, based only on the equations described above, allocates the contribution of the dimer $(b_k, b_{k+1})$ to the release energy between the term $\varepsilon(b_k, b_{k+1})$ and the term $\omega_k$, nor even how the algorithm allocates the value of a quotient between the numerator and the denominator thereof. To put it another way, in the best of cases, as it stands, only the term $\omega_k \cdot \varepsilon(b_k, b_{k+1})$ is relevant. The same comment applies obviously to the terms $\omega_k^* \cdot \varepsilon^*(b_k, b_{k+1})$. Furthermore, still regarding the identification, note that these terms occur in exponentials which are present in fraction denominators, which makes the identification even more difficult.

Moreover, even if there were an identification algorithm capable of relevantly differentiating the different terms, only the terms $\omega_k$ and $\varepsilon(b_k, b_{k+1})$ can be used. The terms $\omega_k^*$ and $\varepsilon^*(b_k, b_{k+1})$, for their part, are valid only for the learning DNA chips. In effect, a particular value for the corresponding term $\omega_k^* \cdot \varepsilon^*(b_k, b_{k+1})$ is obtained for the defects arising for the learning chip. If the subsequent design of a new DNA chip is now considered, consisting in testing by computer candidate probes on the basis of the particular values of the terms obtained on the learning chips, essentially the new chip to be designed is different from the learning chip or chips. This means that the mismatches have a high probability, even a certainty, of being different from those existing in the learning chip. The value of the term $\omega_k^* \cdot \varepsilon^*(b_k, b_{k+1})$ is not therefore valid. In effect, the terms $\omega_k^*$ and $\varepsilon^*(b_k, b_{k+1})$ effect an average of the non-specific hybridizations without specifically knowing the mismatches which actually arise on the DNA chip. Thus, the parameters estimated from a sample cannot be generalized.

Other more complex models have been proposed, such as, for example, that described in the document "*An improved physico-chemical model of hybridization on high-density oligonucleotide microarrays*" by Naoaki Ono et al., Bioinformatics, vol. 24, No. 10, 2008, which also leans on this same approach for modeling the non-specific hybridizations.

However, generally, the models of the prior art pose great problems of identification, and consider the mismatches without differentiation, and therefore too irrelevantly, for the values of the parameters corresponding to the mismatches to be able to be reused subsequently in a DNA chip design phase. There is therefore not currently any model of the affinity of a probe with a target that leads to the effective design of a DNA chip.

DESCRIPTION OF THE INVENTION

The aim of the invention is to propose an accurate modeling of the affinity between a probe and a target whether it be a perfect hybridization (with no mismatch) or a hybridization with one or more mismatches.

To this end, the subject of the invention is a method for estimating the affinity $\phi$ of a first DNA strand, or "probe", to be hybridized with a second DNA strand, or "target", to form a hybrid of length $L_{bp}$, the method comprising:

- in each division of a set of M divisions of the hybrid, counting the number of times in which each hybrid of a set of P DNA strand hybrids is present in the division, said hybrids being of length k less than the length $L_{bp}$, or "k-hybrids";
- for each combination of mismatches of a set of L combinations of mismatches in a hybrid of length $L_{bp}$, determining whether said pair of mismatches is present in said hybrid; and
- calculating the affinity $\phi$ according to the relation:

$$\phi = \sum_{m=1}^{M} \sum_{p=1}^{P} x_{m,p} \cdot \hat{\beta}_{m,p} + \alpha$$

expression in which:
- $\forall (m,p) \in [1,M] \times [1,P]$, $\hat{\beta}_{m,p}$ is a predetermined scalar quantifying the contribution to the affinity $\phi$ of the $p^{th}$ k-hybrid of the set of P k-hybrids when this $p^{th}$ k-hybrid is present in the $m^{th}$ area of said division, and $x_{m,p}$ is the number of times in which this $p^{th}$ k-hybrid is counted for said hybrid in the $m^{th}$ area of said division; and a is a real term.

In other words, the affinity model is based directly on the true composition of the probe/target hybrids and directly takes into account the influence of sub-hybrids contained in the hybrid. This way, each mismatch between the probe and the target is explicitly and individually taken into account. This notably makes it possible to determine the affinity of a probe with its specific target, but also the affinity of the probe with a target upon a cross-reaction, and therefore in the presence of mismatches.

Furthermore, a model according to the invention is linear, unlike the models of the prior art which consider an affinity which is proportional to an exponential. Because of the linearity of the model, it is possible to implement identification algorithms based on convex problems. Since this is known per se, this type of identification is the most robust, fastest and most accurate.

The estimation of the affinity, implemented by computer, is done for example following the sequencing of one or two DNA strands or the sequencing of an RNA or of a DNA comprising the strand, sequencing which produces a numeric sequence of nitrogenous bases of said strand, sequence stored in a computer memory. The counting of the k-hybrids, for its part, corresponds to a measurement on the structure of the double strand derived from the hybridization of the first and second strands, a measurement which is then processed to estimate the affinity. For example, the method comprises a) the sequencing of the first DNA strand so as to produce a first numeric sequence of nitrogenous bases forming said strand, b) the determination of a second numeric sequence of nitrogenous bases forming a second DNA strand (e.g. by sequencing of a known strand, by ad-hoc construction of the sequence, by a determination of the strictly complementary strand in the context of the affinity of a perfect hybrid, etc.), c) the counting of the k-hybrids is then performed on the first and second hybridized numeric sequences.

The first strand is for example a DNA chip probe and the second strand is a portion of a target transcript of the DNA chip, which notably makes it possible to test the quality of the DNA chip by determining the affinity. In another exemplary application, the first strand is a messenger RNA strand, for example a virus, and the second strand is a strand whose function is to be attached specifically and stably with the first strand to block the transcription thereof (gene therapy through the use of a so-called "antisense" strand).

Knowing the affinity of the hybrid thus makes it possible to characterize the effectiveness of the therapy.

According to one embodiment:

$$\alpha = \sum_{l=1}^{L} y_l \cdot \hat{\delta}_l + \pi$$

expression in which $\forall l \in [1,L]$, $\hat{\delta}_l$ is a predetermined scalar quantifying the contribution to the affinity $\phi$ of said $l^{th}$ pair of mismatches, $\gamma_l = 1$ if said $l^{th}$ pair of mismatches is present in said hybrid and $\gamma_l = 0$ otherwise, $\pi$ is a real number, advantageously equal to 0.

More particularly the method comprises:
- for each pair of a set of N learning pairs each comprising a first and a second DNA strands capable of together forming a hybrid of length $L_{bp}$, bringing together a quantity of the first DNA strand of said pair with a quantity of the second DNA strand of said pair, and measuring an intensity $I_n$ representative of the quantity of DNA strand hybrids formed following this bringing together, the hybrids of said calibration pairs comprising at least one times each k-hybrid of the set of P k-hybrids; and
- calculating a vector $\hat{B} \in \mathbb{R}^{P \cdot M}$, a vector $\hat{\Theta} \in \mathbb{R}^{N}$ and a vector $\hat{\Delta} \in \mathbb{R}^{L}$ minimizing a distance D between a vector $I = (I_1 \ldots I_n \ldots I_N)^T \in \mathbb{R}^{N}$ of the measured intensities and a vector $M = (M_1 \ldots M_n \ldots M_N)^T \in \mathbb{R}^{N}$ of prediction of the vector I of the measured intensities, said calculation being performed by solving an optimization problem according to the relations:

$$(\hat{B}, \hat{\Theta}, \hat{\Delta}) = \arg\min_{B,\Theta,\Delta} D(I, M)$$

$$\forall n \in [1, N], M_n = \theta_n \cdot (X_n \cdot B + Y_n \cdot \Delta)$$

expressions in which:
- $\Theta = (\theta_1 \ldots \theta_n \ldots \theta_N)^T$ is a vector of $\mathbb{R}^N$, in which $\forall n \in [1,N]$, $\theta_n$ is a scalar coding a quantity of the first and/or second DNA strands brought together for the $n^{th}$ calibration pair;
- $\forall n \in [1,N]$, $X_n = (X_{n,1} \ldots X_{n,m} \ldots X_{n,m})$ is a row matrix of predetermined design of $\mathbb{R}^{P.M}$, in which $\forall m \in [1,M]$, $X_{n,m} = (x_{n,m,1} \ldots x_{n,m,p} \ldots x_{n,m,P})$ is a row matrix of $\mathbb{R}^P$ and $\forall p \in [1,P]$, $x_{n,m,p}$ is the number of times in which the $p^{th}$ k-hybrid is present in the $m^{th}$ area of said division for the hybrid formed by the first and second DNA strands of the $n^{th}$ calibration pair;
- $B = (B_1 \ldots B_m \ldots B_M)^T$ is a vector of $\mathbb{R}^{P.M}$, in which $\forall m \in [1,M]$, $B_m = (\beta_{m,1} \ldots \beta_{m,p} \ldots \beta_{m,P})^T$ is a vector of $\mathbb{R}^P$, with $\forall p \in [1,P]$, $\beta_{m,p}$ is a scalar quantifying the contribution to the affinity of a hybrid of length $L_{bp}$ of the $p^{th}$ k-hybrid of the set of P k-hybrids when this $p^{th}$ k-hybrid is present in the $m^{th}$ area of said division;
- $\forall n \in [1,N]$, $Y_n = (y_{n,1} \ldots y_{n,l} \ldots y_{n,L})$ is a row matrix of predetermined design of $\mathbb{R}^L$, in which $\forall l \in [1,L]$, $y_{n,l} = 1$ if the $l^{th}$ pair of mismatches is present in the hybrid formed by the first and second DNA strands of the $n^{th}$ calibration pair; and
- $\Delta = (\delta_1 \ldots \delta_l \delta_L)^T$ is a vector of $\mathbb{R}^L$, in which $\forall l \in [1,L]$, $\delta_l$ is a scalar quantifying the contribution to the affinity of a hybrid of length $L_{bp}$ of said $l^{th}$ pair of mismatches.

According to one embodiment:
the k-hybrids have a length k of between 2 and 7; and
the number M of areas of said division is between 2 and 25-k.

More particularly, the number M of areas is between 3 and 15. The k-hybrids notably have a length k of between 3 and 5.

According to a variant, the solving of the optimization problem is resolved subject to the additional constraint according to the relation:

$$\sum_{i=1}^{I} \theta_i^2 = \alpha$$

in which I is the number of different RNAs, $\alpha$ is a predetermined positive scalar, advantageously equal to I.

According to a variant, the optimization problem is solved iteratively:
by setting, on the iteration i, the vectors B, $\Delta$ to their values calculated on the preceding iteration i−1 and by solving the optimization problem according to the relations:

$$(\hat{\Theta}(i)) = \arg\min_{\Theta(i)} D(I, M(i))$$

$$\forall n \in [1, N], M_n(i) = \theta_n(i) \cdot (X_n \cdot B(i-1) + Y_n \cdot \Delta(i-1))$$

by setting, on the iteration i+1, the vector $\Theta$ to its value calculated on the iteration i, and by solving the optimization problem according to the relations:

$$(\hat{B}(i+1), \hat{\Delta}(i+1)) = \arg\min_{B(i+1),\Delta(i+1)} D(I, M(i+1))$$

$$\forall n \in [1, N], M_n(i+1) = \theta_n(i) \cdot (X_n \cdot B(i+1) + Y_n \cdot \Delta(i+1))$$

More particularly, the first iteration is performed by setting $\forall n \in [1,N]$, $X_n \cdot B(1) + Y_n \cdot i(1) = 1$ Also a subject of the invention is a method for estimating, implemented by computer, the contributions $\hat{\beta}_{m,p}$ of hybrids of a set of P DNA strand hybrids of length k, or "k-hybrids", to the affinity of a DNA strand hybrid of length $L_{bp}$, comprising:
for each pair of a set of N learning pairs each comprising a first and a second DNA strands capable of together forming a hybrid of length $L_{bp}$, bringing together a quantity of the first DNA strand of said pair with a quantity of the second DNA strand of said pair, and measuring an intensity $I_n$ representative of the quantity of DNA strand hybrids formed following this bringing together, the hybrids of said calibration pairs comprising at least one times each k-hybrid of the set of P k-hybrids; and
calculating a vector $\hat{B} \in \mathbb{R}^{P.M}$, a vector $\hat{\Theta} \in \mathbb{R}^N$ and a vector $\hat{\Delta} \in \mathbb{R}^L$ minimizing a distance D between a vector $I = (I_1 \ldots I_n \ldots I_N)^T \in \mathbb{R}^N$ of the measured intensities and a vector $M = (M_1 \ldots M_n \ldots M_N)^T \in \mathbb{R}^N$ of prediction of the vector I of the measured intensities, said calculation being performed by solving an optimization problem according to the relations:

$$(\hat{B}, \hat{\Theta}, \hat{\Delta}) = \arg\min_{B,\Theta,\Delta} D(I, M)$$

$$\forall n \in [1, N], M_n = \theta_n \cdot (X_n \cdot B + Y_n \cdot \Delta)$$

expressions in which:
- $\Theta = (\theta_1 \ldots \theta_n \ldots \theta_N)^T$ is a vector of $\mathbb{R}^N$, in which $\forall n \in [1,N]$, $\theta_n$ is a scalar coding a quantity of first and/or of second DNA strands brought together for the $n^{th}$ calibration pair;
- $\forall n \in [1,N]$, $X_n = (X_{n,1} \ldots X_{n,m} \ldots X_{n,M})$ is a row matrix of predetermined design of in which $\mathbb{R}^{P.M}$, in which $\forall m \in [1,M]$, $X_{n,m} = (x_{n,m,1} \ldots x_{n,m,p} \ldots x_{n,m,P})$ is a row matrix of $\mathbb{R}^P$ and $\forall p \in [1,P]$, $x_{n,m,p}$ is the number of times in which the $p^{th}$ k-hybrid is present in the $m^{th}$ area of said division for the hybrid formed by the first and second DNA strands of the $n^{th}$ calibration pair;
- $B = (B_1 \ldots B_m \ldots B_M)^T$ is a vector of $\mathbb{R}^{P.M}$, in which $\forall m \in [1,M]$, $B_m = (\beta_{n,1} \ldots \beta_{m,p} \ldots \beta_{m,P})^T$ is a vector of $\mathbb{R}^P$, with $\forall p \in [1,P]$, $\beta_{m,p}$ is a scalar quantifying the contribution to the affinity of a hybrid of length $L_{bp}$ of the $p^{th}$ k-hybrid of the set of P k-hybrids when this $p^{th}$ k-hybrid is present in the $m^{th}$ area of said division;
- $\forall n \in [1,N]$, $Y_n = (Y_{n,1} \ldots y_{n,l} \ldots Y_{n,L})$ is a row matrix of predetermined design of $\mathbb{R}^L$, in which $\forall l \in [1,L]$, $y_{n,l} = 1$ if the $l^{th}$ pair of mismatches is present in the hybrid formed by the first and second DNA strands of the $n^{th}$ calibration pair; and
- $\Delta = (\delta_1 \ldots \delta_l \ldots \delta_L)^T$ is a vector of $\mathbb{R}^L$, in which $\forall l \in [1,L]$, $\delta_l$ is a scalar quantifying the contribution to the affinity of a hybrid of length $L_{bp}$ of said $l^{th}$ pair of mismatches.

Another subject of the invention is a computer program product stored on a computer-usable computing medium comprising instructions for the execution of a method as claimed in any one of the preceding claims.

Another subject of the invention is a method for fabricating a DNA chip comprising copies of a DNA strand, or probe, capable of forming a hybrid of length $L_{bp}$ with a target strand of nucleic acid, notably of DNA, of length greater than $L_{bp}$ without mismatch, said method comprising:
- identifying a set of portions of length $L_{bp}$, on the target DNA strand;
- for each identified portion of the target DNA strand, "or candidate target":
  - determining the complementary DNA strand, or "candidate probe", and calculating a first affinity ϕ of the candidate probe and target by implementing an affinity estimation method, notably of the abovementioned type;
  - calculating a second affinity ϕ of the candidate probe with each element of a set of reference nucleic strands not comprising the candidate target by implementing an affinity estimation method, notably of the abovementioned type;
- selecting, from the determined candidate probes, at least one probe
  - the first affinity ϕ is above a predetermined first threshold; and
  - each of the second affinities ϕ is below a second threshold strictly lower than the first threshold;
- fabricating the DNA chip with each selected candidate probe.

In other words, it has been found that it is possible to design a DNA chip by explicitly taking into account only the affinity of the probes. While only the affinity is explicitly taken into account, the method according to the invention does however also take into account, naturally but implicitly, the specificity of the probes. In effect, according to the method the probe retained according to the threshold criteria described above is necessarily specific.

It is not therefore necessary to develop specificity models and/or implement specific tests for evaluating the latter. The design of the chip according to the invention is therefore greatly simplified. Thus, by using the affinity model according to the invention, the first tests have resulted in DNA chips of quality at least equal to that of the prior art.

BRIEF DESCRIPTION OF THE FIGURES

The invention will be better understood on reading the following description, given purely by way of example, and in relation to the attached figures in which:

FIGS. 7 to 9 are diagrams illustrating the choice of candidate probes for a DNA chip;

FIGS. 11A to 11D are graphs illustrating the variation of the coefficient of determination of the affinity model according to the invention as a function of the length k of the k-hybrids and the number M of divisions of a probe/target hybrid;

FIGS. 14A to 14B are graphs illustrating measured intensities as a function of predicted intensities respectively on two DNA chips;

FIG. 14C is a box diagram on the determination coefficient corresponding to FIGS. 14A and 14B;

FIGS. 15A to 15G are graphs illustrating the accuracy of the measurements of a DNA chip designed according to the method according to the invention.

DETAILED DESCRIPTION OF THE INVENTION

A) System for Estimating Affinity and Selecting Probes of a DNA Chip

Figure 1:
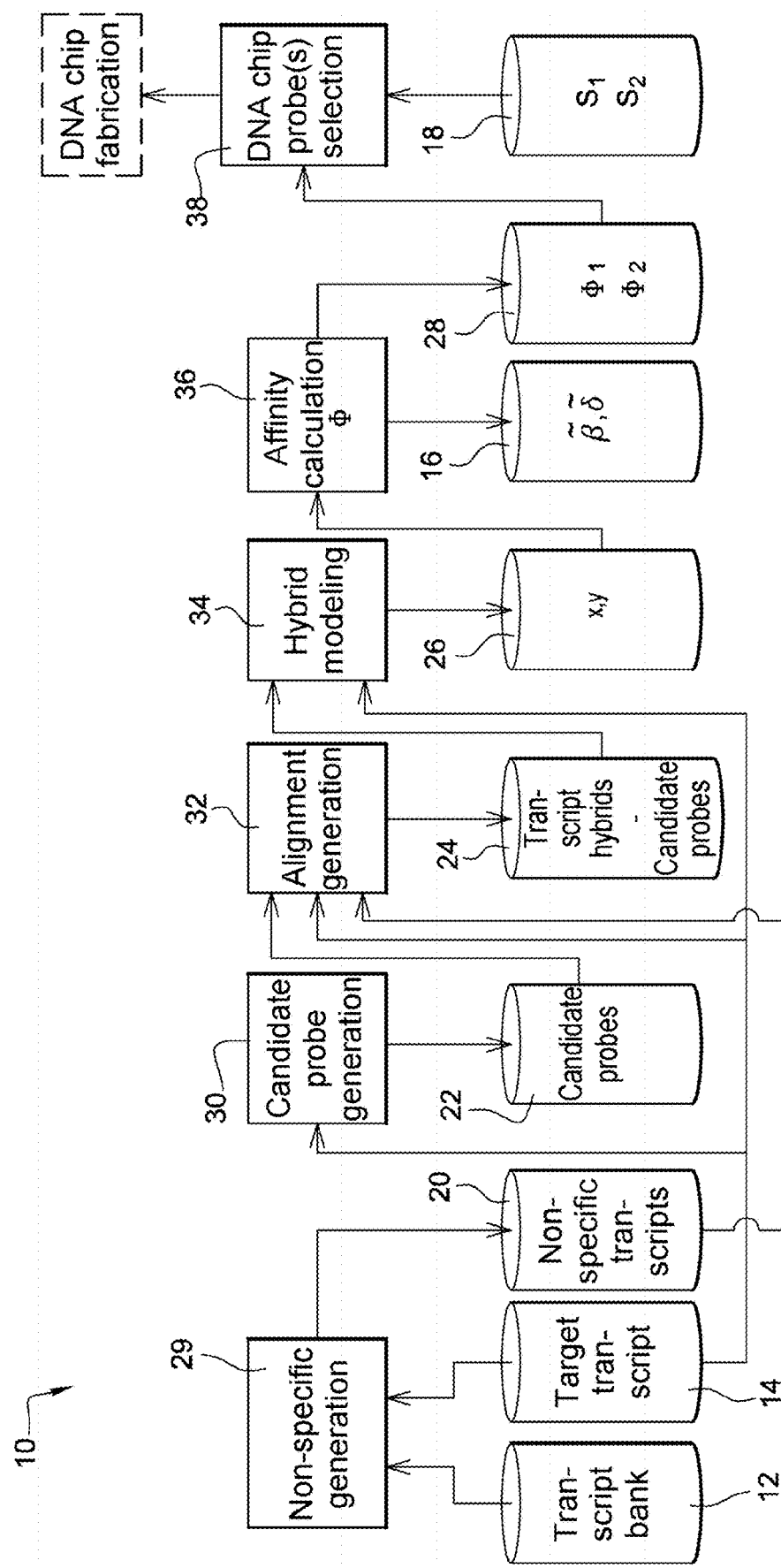
FIG. 1 is a functional schematic view of an information processing unit implementing a probe design method for a DNA chip according to the invention.

FIG. 1 is a schematic view of the functional blocks implemented by an information processing unit 10, for example a personal computer, or any device based on a microprocessor, RAM, ROM and mass memories, etc., capable of implementing software comprising the computing instructions necessary to the implementation of the method, for selecting probes of a DNA chip measuring the level of expression of a particular transcript, or "target" transcript. This selection, of which the unit 10 implements a particular embodiment, aims to identify one or more specific probes of length $L_{bp}$ which are specific and affine with the target transcript, and which are not, or are weakly, affine with other transcripts, or "non-specific" transcripts, the selected probes then being used for the fabrication of the DNA chip.

As an example, the DNA chip is designed to detect an endogenous retrovirus transcript present in the human genome, or "HERV" which stands for "human endogenous retroviruses", and an LTR retrotransposon transcript, an ancestor of the infectious retroviruses, or "MaIR" which stands for "Mammalian-Apparent Long-Terminal Repeat Retrotransposon". The HERV/MarlR elements represent up to 8% of the human genome, or approximately 400 000 elements or loci that can each produce 0, 1 or several transcripts of a length that can range up to 10 000 nitrogenous bases. By convention, these elements are referred to as "HERV/MarlR". It is known that designing a DNA chip targeting a particular HERV/MalR transcript is very difficult because of the very many DNA sequences called "repeats" that the HERV/MalR elements share, that is to say sequences that are identical or phylogenetically very close to one another present at very many points in the human genome.

The computing unit 10 comprises:
- a first memory block 12 storing a numeric bank of HERV/MalR loci, or a set of more than 400 000 numerical sequences of nitrogenous bases corresponding to the potential HERV/MarlR transcripts, e.g. previously sequenced in a manner known per se;
- a second memory block 14 storing the numeric sequence coding the target HERV/MarlR transcript, for example entered by the designer of the DNA chip;
- a third memory block 16 storing a set $\{\hat{\beta}_{m,p}, \hat{\delta}_l\}$ of coefficients $\hat{\beta}_{m,p}$ and $\hat{\delta}_l$ quantifying contributions to the affinity of k-hybrids and of pairs of mismatches, as will be explained in more detail herein below;

a fourth memory block 18 storing thresholds $S_1$, $S_2$ parameterizing DNA chip probe selection rules; and memory blocks 20, 22, 24, 26, 28 storing intermediate probe selection results.

The unit 10 also comprises computation blocks, for example software modules implemented on a computer, in particular:

a block 29 for generating a set of numerical sequences of coding nitrogenous bases for the non-specific transcripts. The block 28 creates, from the bank of transcripts 12, a new set of numerical sequences of nitrogenous bases, by removing from it the target transcript stored in the block 14. This new set therefore codes the non-specific transcripts for which probes of weak affinity are sought, and is stored in the memory block 20. There are many ways of generating the set of non-specific transcripts. For example, the block 28 may be omitted when the set of the bank 12 contains only these transcripts. In order to lighten the notations, reference herein below is made indifferently to the sequences corresponding to transcripts or to the transcripts themselves;

a block 30 for generating candidate probes for the target transcript. Preferably, the block 30 identifies each subsequence of the length $L_{BP}$ of the target transcript at each position thereof, then determines, for each of these subsequences, the strictly complementary sequence in terms of nitrogenous bases. These complementary subsequences form the "candidate" probes for the DNA chip and are stored in the memory block 22. By analogy, the target transcript portion corresponding to a candidate probe is referred to by the expression "candidate target". Many other candidate probe selection rules can of course be implemented. For example, some portions of the target transcript can be disregarded if it is known beforehand that they cannot give appropriate probes for the DNA chip;

an alignment block 32 forming hybrids between each candidate probe of the memory block 22 and the non-specific transcripts of the memory block 20. More particularly, the block 32 identifies the hybrids comprising at most two mismatches. To do this, the block 32 identifies the hybrids having a maximum number of pairs of matched bases, by introducing, as necessary, a mismatch of gap type. The hybrids thus identified are stored in the memory block 26. The limiting of the number of defects makes it possible to speed up the method according to the invention and to limit the number of coefficients $\{\hat{\beta}_{mp}, \hat{\delta}_l\}$ necessary to the computation of the affinity. The inventors have in fact noted that, from three mismatches, the affinity of a probe with a transcript drops, the intensity of a DNA chip corresponding to the probe/transcript hybrid being moreover buried in the background noise. This observation is corroborated by the study "*Custom human endogenous retroviruses dedicated microarray identifies self-induced HERV-W family elements reactivated in testicular cancer upon methylation control*" by Gimenez et al., Nucleic Acids Research, April 2010, vol. 38(7): 2229-2246. For example, the module 32 implements the "BWA" alignment software described in the document "*Fast and accurate long-read alignment with Burrows-Wheeler transform*", by Li H. et al, Bioinformatices, vol. 26(5): 589-595, and that can be downloaded as indicated in that document;

a block 34 for modeling each hybrid stored in the memory block 24 and each hybrid formed from a candidate probe and its target transcript using "k-hybrids" and pairs of mismatches, in a manner described herein below. This modeling produces a set $\{x_{m,p}, y_l\}$ of variables $x_{m,p}$ and $y_l$ for each hybrid, coefficients which are stored in the memory block 24;

a computation block 36 which computes, for each set $\{x_{m,p}, y_l\}$ stored in the memory block 26, an affinity $\phi$ of the corresponding hybrid as a function of the coefficients $\hat{\beta}_{m,p}$ and $\hat{\delta}_l$ stored in the memory block 16, in a manner explained herein below. The computed affinities $\phi$ are then stored in the memory block 28. Note that, for each candidate probe, several affinities $\phi$ are computed, an affinity $\phi_1$ for the target transcript of the probe and a plurality of affinities $\phi_2$ for the non-specific transcripts; and a selection block 38 which selects at least one probe for which the computed affinities $\phi$, stored in the memory block 28, bear out the selection rules parameterized by the thresholds $S_1$, $S_2$ stored in the memory block 18, in a manner described herein below.

B) Estimating the Affinity of a Probe with a Transcript

Figure 2:
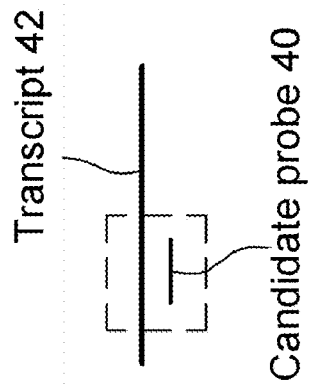
FIGS. 2 to 4 are diagrams illustrating the subdivision of a probe/target hybrid into k-hybrids.
Figure 3:
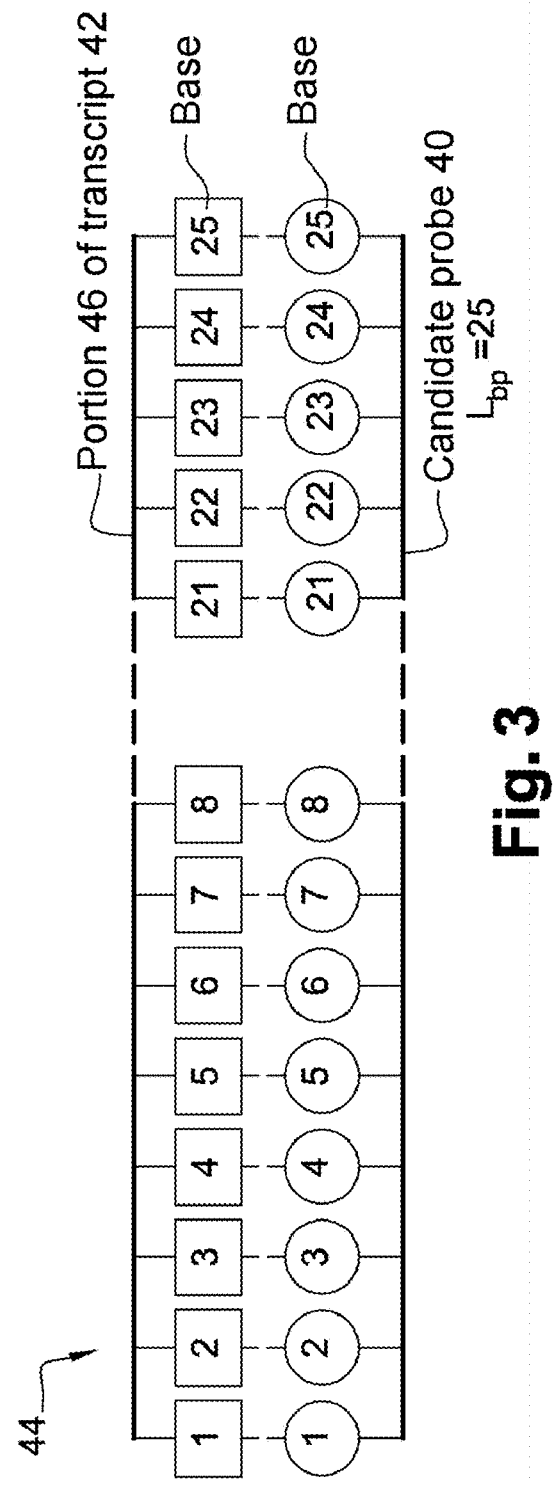
Figure 4:
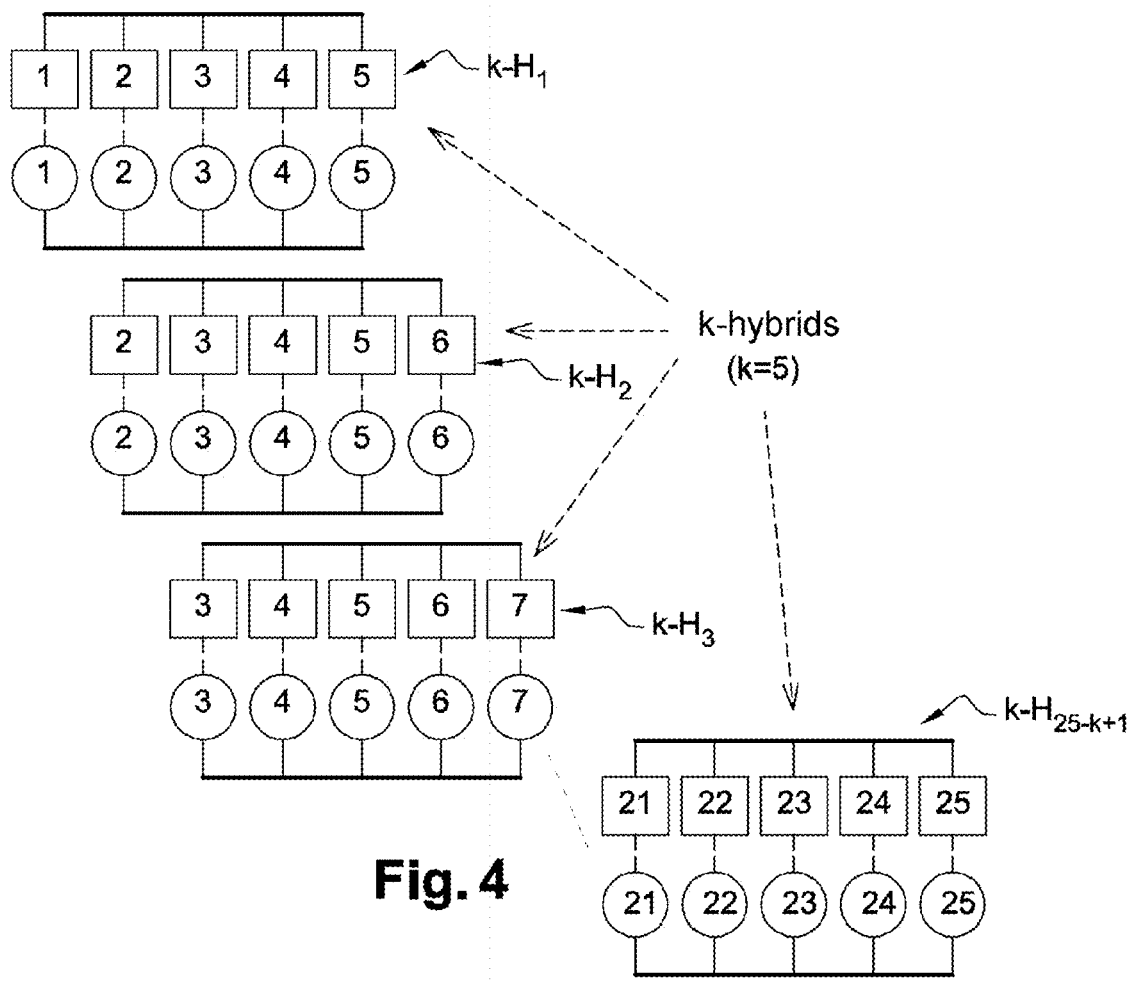
Figure 5:
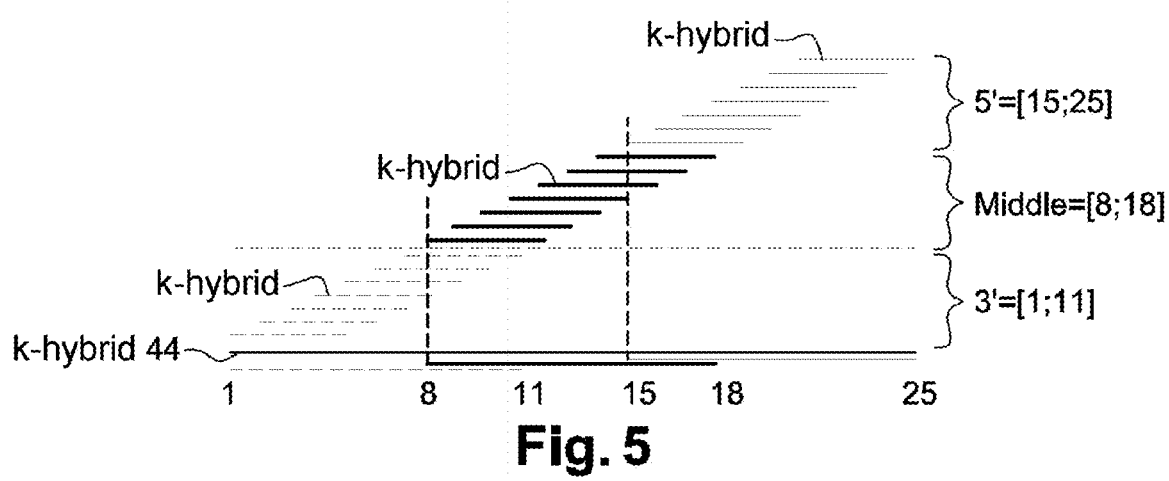
FIG. 5 is a diagram illustrating the subdivision into three areas of a probe/target hybrid.

The selection of probes for a DNA chip implemented by the unit 10 being partly defined by the modeling of the affinity $\phi$ according to the invention, the latter is first of all detailed in relation to FIGS. 2 to 6. In particular, to estimate the affinity $\phi$ of a candidate probe 40 with a transcript 42 on a particular position thereof, as illustrated in FIG. 2, only the hybrid formed by the probe 40 and the portion of the transcript 42 to which the probe 40 is attached is considered. This hybrid, illustrated in FIG. 3 under the reference 44, therefore comprises the probe 40, of a length $L_{bp}$ equal for example to 25 bases, hybridized with the portion of transcript 46 of the same length. By convention, the bases of the probe and of the portion of the transcript are numbered from 1 to 25 starting from the left. According to this same convention, the position of a pair of matched bases in the hybrid is similarly numbered between 1 and 25 starting from the left.

For the estimation of the affinity $\phi$ of the probe 40 with the portion of transcript 46, the set of portions k–$H_1$, k–$H_2$, k–$H_3$, . . . k–$H_{25-k+1}$ of the hybrid of length k=5 bases is identified, these portions of length k being designated by the expression "k-hybrids". For a hybrid of length $L_{bp}$, a total of $L_{bp}$–k+1"k-hybrids" is therefore identified. The model of the affinity $\phi$ according to the invention computes the affinity $\phi$ as a function of the contribution of each identified k-hybrid, the contribution of a k-hybrid also depending on the position thereof in the hybrid.

The position of a k-hybrid can be the precise position in the hybrid, for example determined by the position of the pair of matched bases of the k-hybrid leftmost in the hybrid. This so-called "any position" model therefore leads to considering $L_{bp}$–k+1 different positions. However, the number of positions influences the number of parameters of the model, and therefore influences the computing resources necessary to the implementation thereof, as well as the quantity of learning data needed.

Advantageously, the number of positions of a k-hybrid in the hybrid is reduced by dividing the hybrid into a limited number M of areas. For example, by referring to FIG. 5, the hybrid 44 is divided into 3 areas called "3", "middle" and "5" of identical width. The set of the k-hybrids present in the hybrid 44 is illustrated by the segments of length k=5, offset by one base relative to the others. According to this division into three areas, a k-hybrid therefore belongs to the first area "3" when its leftmost pair of hybridized bases lies between the positions 1 and 7 in the hybrid, to the second area "middle" when said pair of bases lies between the positions 8 and 14 in the hybrid, and to the third area "5" when said pair of bases lies between the positions 15 and 21 in the hybrid. A set of identified k-hybrids is thus obtained for each area, namely, respectively, the sets: $\{k-H_1, k-H_2, \ldots, k-H_7\}_{3'}$, $\{k-H_8, k-H_9, \ldots, k-H_{14}\}_{Middle}$, $\{k-H_{15}, k-H_{16}, \ldots, k-H_{21}\}_{5'}$.

The contribution to the affinity $\phi$ of a k-hybrid in an area of the hybrid is moreover computed beforehand, in a way that will be explained in more detail herein below, and stored in the coefficients $\hat{\beta}_{m,p}$ of the memory block 16. More particularly, having an alphabet of 5 elements (A, C, T, G, gap) for a length k, there are P different configurations k–H$^1$, k–H$^2$, k–H$^3$, ... k–H$^p$, k–H$^P$ for a k-hybrid. For each of these configurations k–H$^p$ a contribution $\hat{\beta}_{3',p}$ for the first area "3", a contribution $\hat{\beta}_{Middle,p}$ for the second area "middle" and a contribution "$\hat{\beta}_{5',p}$" for the third area "5" are computed beforehand.

A first variant of the estimation of the affinity $\phi$ according to the invention then consists of:
a. for each k-hybrid configuration k–H$^p$, in counting:
   the number of times $x_{3',p}$ in which this configuration appears in the set $\{k-H_1, k-H_2, \ldots, k-H_7\}_{3'}$ of the first area "3";
   the number of times $x_{Middle,p}$ in which this configuration appears in the set $\{k-H_8, k-H_9, \ldots, k-H_{14}\}_{Middle}$ of the second area "Middle";
   the number of times $x_{5',p}$ this configuration appears in the set $\{k-H_{15}, k-H_{16}, \ldots, k-H_{21}\}_{5'}$ of the third area "5";
b. then in computing the affinity $\phi$ according to the relation:

$$\phi = \sum_{p=1}^{P} x_{3',p} \cdot \hat{\beta}_{3',p} + \sum_{p=1}^{P} x_{Middle,p} \cdot \hat{\beta}_{Middle,p} + \sum_{p=1}^{P} x_{5',p} \cdot \hat{\beta}_{5',p} \quad (1)$$

As can be seen, by explicitly taking into account the structure of a hybrid, the possible mismatches are therefore explicitly taken into account since they are involved in the P different configurations k–H$^1$, k–H$^2$, k–H$^3$, . . . k–H$^p$, . . . , k–H$^P$.

For any number of M areas of the hybrid, including an any-position model, the above equation is easily generalized to the equation:

$$\phi = \sum_{m=1}^{M} \sum_{p=1}^{P} x_{m,p} \cdot \hat{\beta}_{m,p} \quad (2)$$

Moreover, there is a synergy effect between the mismatches present in a hybrid. This synergy effect, also called "interaction", is naturally taken into account in the coefficients $\hat{\beta}_{m,p}$ when the mismatches belong to a same k-hybrid. However, when the mismatches are not included together in a single k-hybrid, and are therefore separated by more than k bases, the affinity model according to the relation (2) does not make it possible to take account thereof. For example, by referring to FIG. 6, mismatches are present at the positions 2, 4 and 7 of the hybrid 44. The pair of defects in positions 2 and 4 and the pair of defects 4 and 7 being separated by less than k=5 bases, the synergy effect of these pairs is therefore taken into account by the subdivision into k-hybrids of the hybrid. By contrast, the defects in positions 3 and 7 being separated by more than k=5 bases, their synergy effect is not taken into account in the estimation of the affinity of the relation (2).

Advantageously, the model of the affinity described previously is complemented by a term taking into account the synergy effect between the mismatches. More particularly, for the given lengths $L_{bp}$ and k, there are L configurations $C_1, C_2, \ldots, C_l, \ldots C_L$ of two mismatches separated by more than k bases, and, for each of these pairs $C_l$, a contribution $\hat{\delta}_l$ to the affinity $\phi$ is computed beforehand, this contribution being stored in the memory block 16.

A second variant of the estimation of the affinity $\phi$ therefore consists also in identifying, in the hybrid, the mismatches separated by more than k bases and:
c. for each configuration $C_l$ of mismatches, determining whether this configuration is present in the pairs identified. If such is the case, a variable $y_l$ is then set equal to 1, and to 0 otherwise,
d. then in computing the affinity $\phi$ according to the relation:

$$\phi = \sum_{m=1}^{M} \sum_{p=1}^{P} x_{m,p} \cdot \hat{\beta}_{m,p} + \sum_{l=1}^{L} y_l \cdot \hat{\delta}_l \quad (3)$$

It will thus be noted that the defects and their precise positions in the hybrid are also taken into account for the computation of the affinity.

C) Method for Selecting DNA Chip Probes

Figure 7:
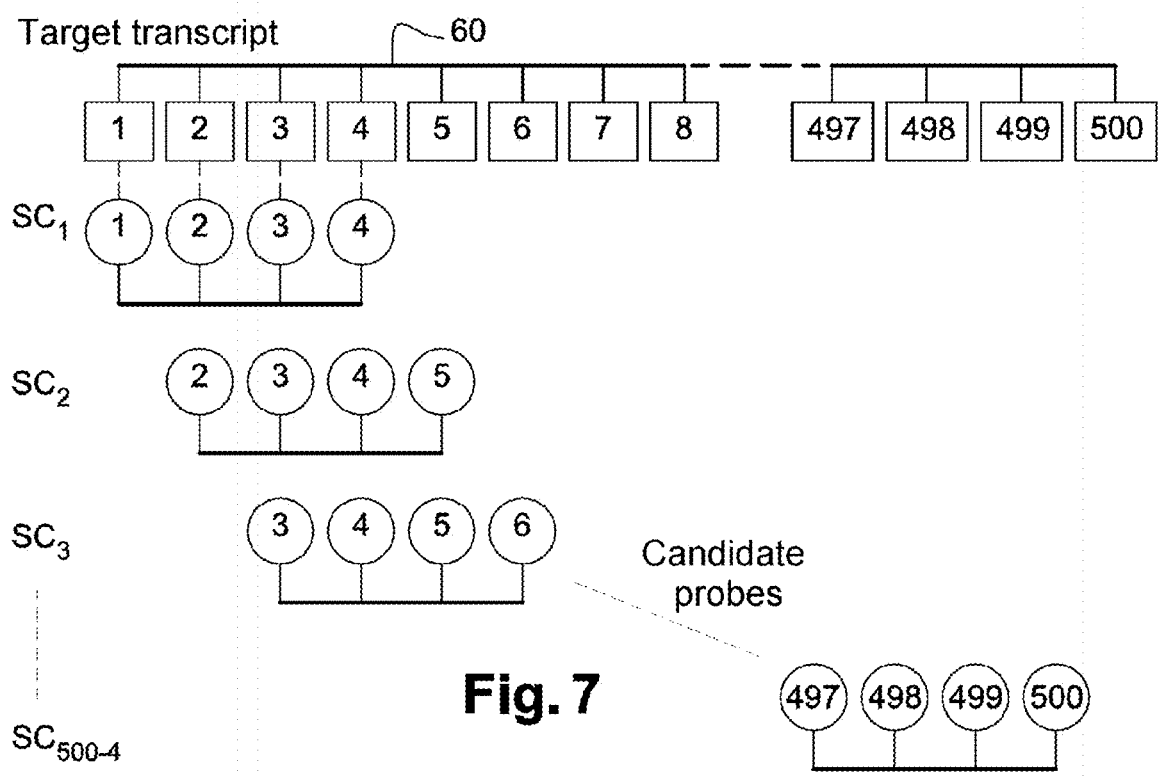

The method for selecting probes for the DNA chip is now described in more detail in relation to FIGS. 7 to 9. These figures illustrate, by way of example and for clarity of the figures, specific and non-specific transcripts of the same length $L_T$, equal to 500 nitrogenous bases, the bases being numbered from 1 to 500. Still in the interest of clarity of the figures, the candidate probes are represented with only 4 bases, their real length $L_{bp}$ being greater, notably between 20 and 100 nitrogenous bases.

Referring to FIG. 7, the module 30 for generating candidate probes identifies each portion of length $L_{bp}$ of the target transcript 60, the portions being offset by one base relative to one another. For each of these portions, the module 30 generates a candidate probe $SC_1, SC_2, \ldots, SC_s, \ldots, SC_{L_T-L_{bp}+1}$ made up of the complementary sequence of said portion. A total of $L_T-L_{bp}+1$ candidate probes is thus generated and stored in the memory block 22.

Referring to FIG. 8, the module 32 for generating alignments identifies, for each non-specific transcript 62 and candidate probe $SC_s$ 64 pair, a set of hybrids comprising at most two mismatches. For example, in FIG. 7, four alignments of this type are identified, respectively at the positions 1, 5, 211 and 497 of the target transcripts. As illustrated in FIG. 9, the modeling module 34 then extracts the hybrids $H_{s,1}, H_{s,5}, H_{s,211}, H_{s,497}$ formed by the candidate probe 64 and portions of the transcript 62 to which it is attached, as described above in relation to FIGS. 2 and 3, and also forms the hybrid $H_{s,PM}$ made up of the candidate probe 64 and of the portion of the specific transcript from which it is derived. Finally, for each hybrid $H_{s,PM}, H_{s,1}, H_{s,5}, H_{s,211}, H_{s,497}$ formed, the module 34 identifies the k-hybrids and the pairs of mismatches and determines, for this hybrid, the coefficients $x_{m,p}$ and $y_l$ as described previously, these parameters being stored in the memory block 26.

The module 36 then next computes the affinities of each hybrid as a function of the coefficients $x_{m,p}$ and $y_l$ stored in the memory block 24, of the contributions $\hat{\beta}_p$ of k-hybrids and of the contributions $\hat{\delta}_l$ of pairs of mismatches stored in the memory block 16, this computation being performed on the basis of the relation (3). The affinities thus computed are then stored in the memory block 28. For each candidate probe $SC_s$ generated from the target transcript there are therefore computed:

a first affinity $\phi_1$ of the candidate probe with its target transcript, forming with the latter a perfect hybrid;

second affinities $\phi_2$ of the candidate probe with the non-specific transcripts, forming with the latter hybrids that are imperfect or not.

Finally, the selection block 38 selects, as a function of the computed affinities $\phi_1$ and $\phi_2$ and of the selection parameters $S_1$ and $S_2$ stored in the memory block 18, at least the candidate probe or probes for which:

a. the first affinity $\phi_1$ is above a first threshold $S_1 > 0$;
b. the second affinities $\phi_2$ are below a second threshold $S_2 > 0$, strictly lower than the first threshold $S_1$.

In a variant, a single threshold $S_1$ can be used. The first affinity Cis that which is above or equal to the threshold $S_1$ and the second affinities $\phi_2$ are those which are strictly below the threshold $S_1$.

The probe or probes thus selected are those which are specific and affine with respect to the target transcript. These probes are then used for the fabrication of the DNA chip whose aim is to measure the level of expression of the target transcript.

Additional selection rules can also be implemented. Notably, in a variant, the selection block 38 also selects the probe or probes for which:

a. the first affinity $\phi_1$ is above the first threshold $S_1$;
b. at most N second affinities $\phi_2$ are above the second threshold $S_2$, N preferably being equal to 1 or 2.

The additional probes selected do not have the specific character of the first probe, and can therefore be hybridized stably with a non-specific transcript. By contrast, there are DNA chips for which the construction and the analysis of the measurements makes it possible to distinguish between a hybridization with a target transcript and a hybridization with a non-specific transcript, or cross-reaction. Similarly, a second rank probe can be retained for the fabrication of the DNA chip when it is known that the target transcript and the non-specific transcript with which it is hybridized have a low or zero probability of being present together in the biological sample that is the subject of the measurement by the DNA chip. By also using these probes in the chip, the sensitivity of the DNA chip is therefore enhanced while retaining a specific character for this chip.

According to the invention, to check the specificity of a probe, a specificity score Spec equal to the difference between the first affinity $\phi_1$ and the greater of the two affinities $\phi_2$ is computed for each probe, that is to say a score according to the relation:

$$\text{Spec} = \phi_1 - \max(\phi_2)$$

D) Learning the Contributions $\hat{\beta}_{m,p}$ and $\hat{\delta}_l$

Figure 10:
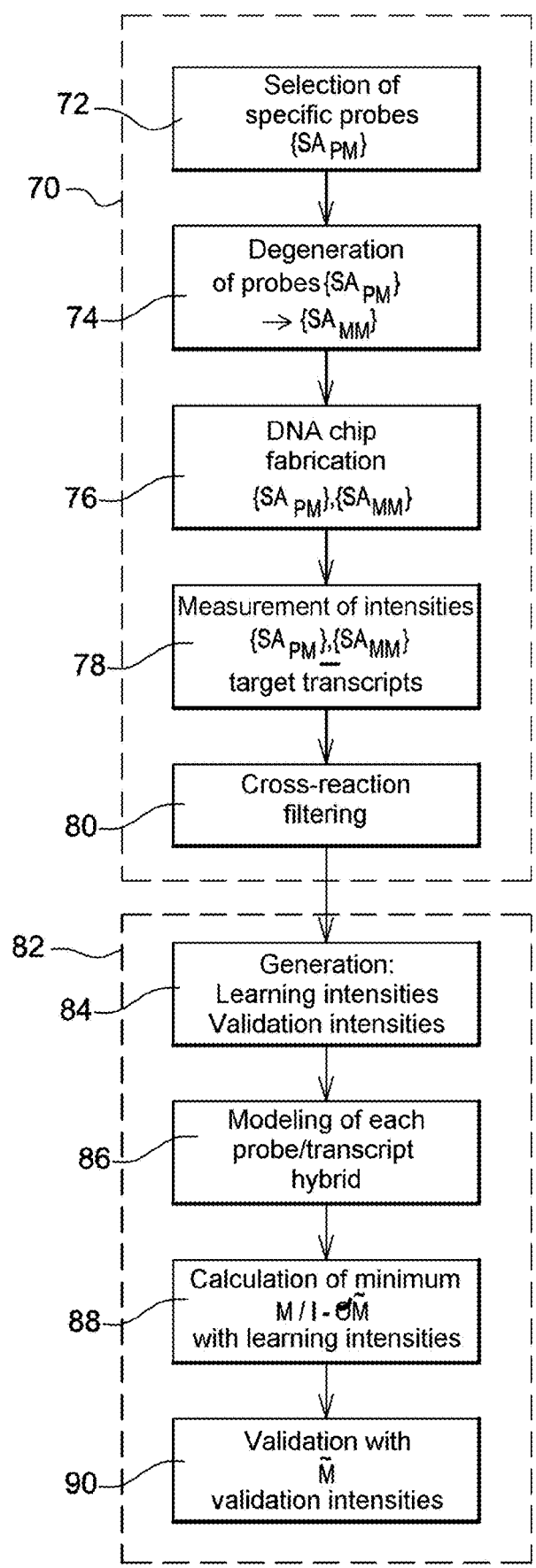
FIG. 10 is a flow diagram of a method for learning the contribution of k-hybrid to the affinity of a probe with a transcript.

FIG. 10 is a flow diagram illustrating a method for learning the coefficients $\hat{\beta}_{m,p}$ and $\hat{\delta}_l$ of the affinity model according to the invention.

This learning begins with the construction, in 70, of experimental learning data on the basis of which to identify the values of the coefficients $\hat{\beta}_{m,p}$ and $\hat{\delta}_l$. More particularly, only "the intensity" of a DNA chip probe or of an analogous device, being an easily accessible experimental data. The experimental data therefore consists of a set $\{I_n\}$ of probe intensities, forming, with transcripts, hybrids which comprise the k-hybrids and the pairs of mismatches corresponding to the parameters $\beta_{m,p}$ and $\hat{\delta}_l$ sought.

However, without a particular measurement, the starting biological sample, the object of the measurement by a DNA chip, comprises several transcripts. Each stable hybrid between a probe and a transcript thus contributes to the intensity of the probe, without it being possible to easily separate each contribution. The first step 72 of construction of the experimental data advantageously consists in selecting the probes for which it is known that they are specific and affine with the only target transcripts from which they have been designed. Notably, the step 72 consists in selecting a first set $\{SA_{PM}\}$ of learning probes derived from conventional cellular genes (or "Protein coding genes"). These probes in effect exhibit little or no cross-reaction. This means most particularly that the intensity of such a probe corresponds substantially to the intensity of the probe with its target transcript, with which it forms a perfect hybrid.

In a next step 74, a second set $\{SA_{MM}\}$ of learning probes is designed from the first set $\{SA_{PM}\}$ by modifying one or two bases of the probes thereof. Because of the very great specificity of a probe of the first set with its target transcript, the inventors have noted that degenerating such a probe, by changing one or two of its bases, leads also to a probe which is very specific with the target transcript. Thus, the intensity of a degenerated probe also corresponds substantially to the intensity of the hybrid that it forms with the target transcript, hybrid which therefore exhibits one or two mismatches. Moreover, as described below, a filtering is implemented to eliminate any cross-reactions which could occur following the degeneration of the probes of the first set $\{SA_{PM}\}$. The first set $\{SA_{PM}\}$ and the second set $\{SA_{MM}\}$ are therefore selected for them both to comprise the P possible configurations of k-hybrids and the L configurations of pairs of mismatches. Preferably, for the robustness of the identification of the coefficients $\beta_{m,p}$ and $\hat{\delta}_l$, these sets are chosen to include each of these configurations several times, and preferably at least 20 times.

Once the learning probes $\{SA_{PM}\}$ and $\{SA_{MM}\}$ are selected, DNA chips are constructed, in 76, from the latter, then the chips are used, in 78, to measure the level of expression of the target transcripts from which the probes $\{SA_{PM}\}$ were designed. A set $\{I\}'$ of probe intensities is therefore obtained. Optionally, a filtering is implemented, in 80, to eliminate the intensities originating from the cross-reactions. Such a filtering is for example described in the document "Model-based analysis of oligonucleotide arrays: expression index computation and outlier detection", by Li et al, Proceedings of the National Academy of Science, vol. 98(1):31-36, November 2006. A set $\{I\}$ of intensities I is then retained. Each intensity/retained therefore has as its single cause a single hybrid, namely that formed from a known probe and a known transcript.

The method for identifying the coefficients $\beta_{m,p}$ and $\hat{\delta}_l$ then continues with the computation thereof as a function of the intensities $\{I\}$ in a step 82.

More particularly, by using the standard notations in the DNA chip field, because of the nature of the probes, and possibly of the filtering of the cross-reactions applied, the intensity $I_{ij}$ of a probe "j" can be modeled according to the relation:

$$I_{ij} = \theta_i \times \phi_j \tag{4}$$

in which $\theta_i$ is the quantity of RNA obtained by amplification of the transcript i targeted by the probe "j" and $\phi_j$ is the affinity between the jth probe and its target transcript.

By combining the relations (3) and (4), the intensity $I_{ij}$ of a probe is therefore rewritten formally:

$$I_{ij} = \theta_i \cdot \left( \sum_{m=1}^{M} \sum_{p=1}^{P} x_{m,p} \cdot \hat{\beta}_{m,p} + \sum_{l=1}^{L} y_l \cdot \hat{\delta}_l \right)_j \tag{5}$$

in which $x_{m,p}$ and $Y_l$ therefore correspond here to the modeling of the hybrid as k-hybrids and pairs of mismatches of the hybrid associated with the intensity $I_{ij}$, and $\hat{\beta}_{m,p}$ and $\hat{\delta}_l$ of the coefficients to be identified.

By adopting a matrix expression, it is shown that the relation (5) is rewritten:

$$I_{ij} = \theta_i \cdot (X \cdot \hat{B} + Y \cdot \hat{\Delta})_j \tag{6}$$

expression in which:

$$X^T = (X_1 \ldots X_m \ldots X_M)^T \in \mathbb{R}^{P.M} \tag{7}$$

$$\forall m \in [1,M], X_m^T = (x_{m,1} \ldots x_{m,p} \ldots x_{m,P})^T \in \mathbb{R}^M \tag{8}$$

$$\hat{B} = (B_1 \ldots B_m \ldots B_M)^T \in \mathbb{R}^{P.M} \tag{9}$$

$$\forall m \in [1,M], B_m = (\beta_{m,1} \ldots \beta_{m,p} \ldots \beta_{m,P})^T \tag{10}$$

$$Y^T = (y_1 \ldots y_l \ldots y_L)^T \in \mathbb{R}^L \tag{11}$$

$$\hat{\Delta} = (\delta_1 \ldots \delta_l \ldots \delta_L)^T \in \mathbb{R}^L \tag{12}$$

in which T is the symbol of the transpose, the notation "$V \in \mathbb{R}^a$" designates a real column vector of $\mathbb{R}^a$, and therefore a column vector comprising a real components.

Note that the right hand term of the relation (6) is nonlinear since it is equal to a product. By contrast, note that the term $X \cdot \hat{B} + Y \cdot \hat{\Delta}$ is linear in the terms $\hat{B}$ and $\hat{\Delta}$ and that the matrices X and Y are known since the hybrid corresponding to the intensity $I_{ij}$ is known.

In a variant of the invention, the quantities of RNA are monitored and known a priori, such that the relation (6) becomes linear. The term $\hat{\Theta}$ of the optimization problem described below is therefore also set and known such that the problem is convex and can therefore be solved more simply. However, monitoring the quantity of RNA is a complex and costly technique. According to a variant described below, a conventional DNA chip measurement technique is implemented, technique that does not make it possible to know a priori the quantities of RNA. These quantities are therefore also identified.

For the record, in the conventional DNA chips, a transcript is targeted by several probes, each forming a perfect hybrid with the transcript. Furthermore, cross-reactions can also take place. This explains why the transcripts and the probes are not usually referenced with the same indices, as is described in the relations (4)-(6). However, because of the nature of the learning probes and of the filtering of the cross-reactions, the intensity amounts to, or is assumed as such, the hybrid formed by a probe and its target transcript such that the notation can be reduced without risk of confusion to a single index "n", a notation which will herein below be employed in order to lighten the relations.

As is conventional in the field of identification, the computation step 82 comprises, in 84, the separation into two sets of the set of intensities {I}, namely into a first learning set {$I_n$} and into a second validation set {$I_q$}. The way in which the experimental data are subdivided, the size of each of these sets and the validation methods are known per se and will not therefore be detailed. For example, the set {$I_n$} comprises ⅔ of the set {I} and the set {$I_q$} the other ⅓ or the validation is implemented according to the "10-fold cross-validation" technique. It will be assumed that the learning set {$I_n$} comprises N intensities, indexed by convention by the integer $n \in [1,N]$. According to the same convention, the set {$SA_n$} of the learning probes and the set of the quantities of RNA {$\theta_n$} associated with the learning set {$I_n$} is likewise indexed by the integer n.

The computation step 82 also comprises a step 86 of modeling of each of the hybrids associated with the intensities I retained, the modeling being identical to that described in relation to FIGS. 3 to 6. For each intensity I of the set {I}, there are therefore obtained a row matrix $X \in \mathbb{R}^{P.M}$ and a row matrix Y of $\mathbb{R}^L$ as described in relation to (7)-(12). In particular, for each intensity $I_n$ of the learning set {$I_n$}, a matrix $X_n$ and a matrix $Y_n$ are obtained.

In a subsequent step 88, an identification algorithm is implemented to minimize a distance D between the vector of the learning intensities $I = (I_1 \ldots I_n \ldots I_N)^T \in \mathbb{R}^N$ and the intensities predicted by the model $M = (M_1 \ldots M_n \ldots M_N)^T \in \mathbb{R}^N$, namely the solving of the optimization problem:

$$(\hat{B}, \hat{\Theta}, \hat{\Delta}) = \arg \min_{B, \Theta, \Delta} D(I, M) \tag{14}$$

$$\forall n \in [1, N], M_n = \theta_n \cdot (X_n \cdot B + Y_n \cdot \Delta) \tag{15}$$

The problem of optimization of the relations (14)-(15) is conventional. Any distance D, also called "cost function", is appropriate, for example the Euclidean norm. Similarly, any type of estimator is appropriate, for example an estimator by nonlinear regression. As can be noted, the problem of the relations (14)-(15) is not convex and therefore comprises several solutions. In a variant, the algorithm seeks several thereof, the one finally retained being for example that exhibiting the lowest estimation error upon the validation with the validation set {$I_q$} or that minimizing a criterion of AIC ("Akaike Information Criterion") or BIC ("Baysian Information Criterion") type.

In a preferred variant, the search space is restricted by adding the constraint:

$$\sum_{i=1}^{I} \theta_i^2 = \alpha \tag{16}$$

in which I is the number of different RNAs deposited on the chip, with a for example equal to I.

The inventors have noted that the problem of optimization of the relations (14), (15) and (16) has a single solution and, in light of the tests carried out, it is probable that this solution is the global optimum, or at the very least a local optimum close to the global optimum.

According to a preferred variant, an iterative solving of the problem of the relations (14), (15) and (16) is implemented:

by setting, on the iteration i, the vectors B, A to their values calculated on the preceding iteration i−1 and by solving the optimization problem according to the relations:

$$(\hat{\Theta}(i)) = \arg\min_{\Theta(i)} D(I, M(i)) \quad (17)$$

$$\forall n \in [1, N], M_n(i) = \theta_n(i) \cdot (X_n \cdot B(i-1) + Y_n \cdot \Delta(i-1)) \quad (18)$$

$$\sum_{i=1}^{I} \theta_i^2 = I \quad (19)$$

by setting, on the iteration i+1, the vector $\Theta$ to its value calculated on the iteration i, and by solving the optimization problem according to the relations:

$$(\hat{B}(i+1), \hat{\Delta}(i+1)) = \arg\min_{B(i+1), \Delta(i+1)} D(I, M(i+1)) \quad (20)$$

$$\forall n \in [1, N], M_n(i+1) = \theta_n(i) \cdot (X_n \cdot B(i+1) + Y_n \cdot \Delta(i+1)) \quad (21)$$

Each of these problems is convex and therefore easily solved. The first iteration is for example performed by setting the affinity of each probe to 1, that is to say $\forall n \in [1,N]$, $X_n \cdot B(1) + Y_n \cdot \Delta(1) = 1$ and therefore by computing a first initial value $\hat{\Theta}(1)$ of the vector $\hat{\Theta}$. In a variant, the first iteration is performed by setting $$\forall o \in [1, O], \theta_i = \frac{1}{I},$$

and by computing first values B(1) and $\Delta(1)$ for the vectors $\hat{B}$ and $\hat{\Delta}$. The iterative solving of the problem is then stopped when the distance D no longer changes, or changes insignificantly, as is known per se.

Advantageously, the problem of optimization of the relations (20)-(21) is solved by implementing a LASSO shrinkage optimization ("Lasso shrinkage method") which consists in adding the constraint according to the relation:

$$\|B\|_1 + \|\Delta\|_1 \leq \lambda \quad (22)$$

in which $\|\cdot\|_1$ is the norm $L_1$ and $\lambda$ is a parameter determined by the LASSO optimization by cross-validation, in a manner known per se. This way makes it possible to reduce the variance of the estimator.

At the end of the step 88, there are therefore obtained a vector $\hat{B}$ and a vector $\hat{\Delta}$, that is to say values $\hat{\beta}_{m,p}$ and $\hat{\delta}_l$ quantifying the contribution of the k-hybrids and of the pairs of mismatches to the affinity $\phi$.

The method then ends, in 90, with the validation of the computed coefficients in order to judge the quality thereof. In particular, the preceding computation step 88 is implemented on the set $\{I_q\}$ of the validation intensities, which makes it possible to identify the corresponding quantities of RNA $\{\theta_q\}$. Each intensity $I_q$ of the set $\{I_q\}$ is then estimated by using the contributions to the affinity computed on the learning intensities $\{I_n\}$. The intensity $I_q$ is thus estimated according to the relation:

$$\hat{I}_q = \theta_q \cdot (X_q \cdot \hat{B} + Y_q \cdot \hat{\Delta}) \quad (23)$$

in which $\hat{I}_q$ is the estimation of the intensity $I_q$, and $X_q$ and $Y_q$ is the model of the hybrid associated with the intensity $I_q$. A step of validation by affinity comparison can also be implemented, as described below in relation to FIG. 12 detailed herein below. The validation step rests in particular on the fact that the quantity of RNA of a transcript is substantially identical from one well to another, which is the case in practice because of the nature of the solution deposited on a DNA chip. Obviously, particular measures must be taken to guarantee this characteristic if the solution is produced according to a protocol different from that usually implemented for the DNA chips, such as, for example, a homogenization of the solution.

Standard statistical analyses are then implemented on the estimation error $I_q - \hat{I}_q$ in a manner that is known per se.

E) Preferred Parameterizations of the Affinity and of the Selection of the Probes Logically, the affinity model according to the invention gains in accuracy as the length k and/or the number M of areas increase. However, the increasing of these parameters poses a certain number of problems, including the need for increasingly significant computer resources because of the increase in the number of parameters of the model and the need to design a set of learning probes that have several copies of long k-hybrids, design which is lengthy and costly.

The inventors carried out tests on the influence of the parameters k and M on the accuracy of the affinity model. Referring to FIGS. 11A to 11D, which illustrate curves of the determination coefficient $R^2$ of the affinity model as a function of the parameters k and M, the inventors observed that the gain in accuracy of the model progresses very little once values for k and M are exceeded. According to these tests, for probes of length $L_{bp} = 25$, the following ranges make it possible to obtain a good accuracy of the model, for a minimal number of parameters and a minimal number of learning probes:

k lies between 2 and 7, notably k lies between 3 and 5; and
M lies between 2 and 25−k, notably M lies between 3 and 15.

F) Results

F.1) Hardware and Construction of the Data

The four examples presented below are based on two DNA chips developed by the applicant. The probes have a length equal to 25 nitrogenous bases.

The first chip, called chip "V2", comprises a first "HERV" compartment developed to measure the HERV transcriptome. This compartment contains 6 multicopy retroviral families corresponding to a little less than 6000 HERV transcripts and is described in the document by Pérot et al. "*Microarray-based sketches of the HERV transcriptome landscape*", PLoS One, 2012; 7(6): e40194, June 2012.

In a second "genes" compartment, in the same format as the preceding one, 513 probe sets are introduced that originate from the DNA chip from the company Affymetrix marketed under the reference "HG_U133_Plus2". The chip HG_U133_Plus2 targets conventional cellular genes and is described in the technical documentation "*Design and Performance of the GeneChip® Human Genome U133_Plus 2.0 and Human Genome U133A 2.0 Array*" accessible on the website of the company Affymetrix.

A third "learning set" compartment is, for its part, designed in order to learn the influence of the mismatches causing cross-reactions between HERV transcripts of a same family. The learning set stems from 20 probe sets of the HG_U133_Plus2 chip, intended by definition to form perfect hybrids with the transcripts that they target. For each probe of these 20 probe sets, 185 degenerated probes, the sequence of which varies by one or two mismatches with the probe, and does so at different positions, have been designed. The learning set therefore contains a set of 37 200 probes.

The chip V2 is therefore a tool for learning affinity prediction models (second compartment) and a tool for validating models learned on a known DNA chip (first compartment).

Figure 6:
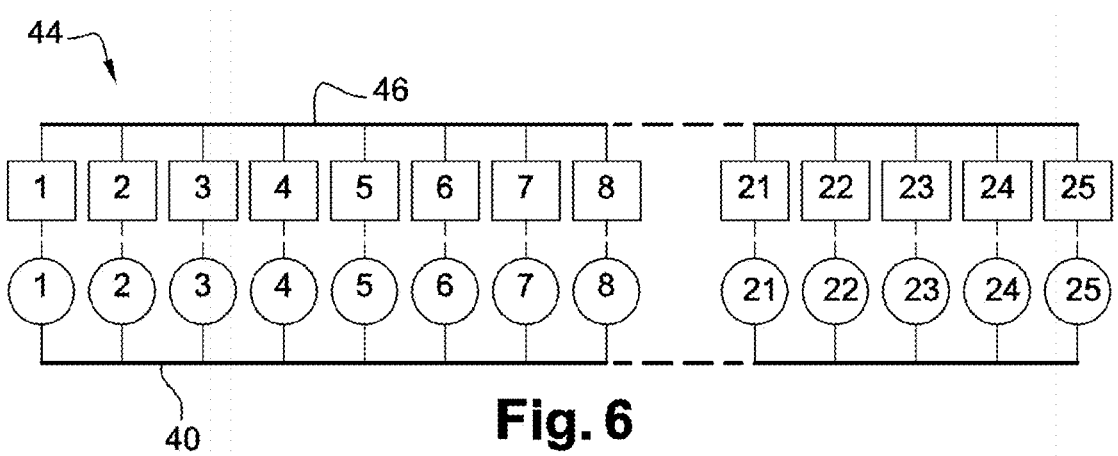
FIG. 6 is a diagram illustrating pairs of mismatches in a probe/target hybrid.

The second DNA chip, called "V3", is a DNA chip designed according to the methodology presented above, namely on the basis of the affinity model of the relation (3) and the probe selection method described in relation to FIGS. 6 to 8. In particular, only the specific and affine probes are retained for the design of this second probe.

The second chip contains approximately 400 000 HERV/MalR elements, organized into several tens of families. The chip V3 is made up of several compartments (probe set) that differ from one another either by the particular elements of the human genome that they target, or by the method of designing the probes that they contain.

The chip V3 notably comprises three compartments "HERV-MalR", "U133_HTA" and "OPTI" which correspond to two types of elements of the human genome and two distinct probe design methods:

the compartments U133_HTA and OPTI target the same 1560 genes, whereas the compartment HERV-MalR targets approximately 400 000 different HERV and MaLR elements of the genes targeted by the compartments U133_HTA and OPTI;

the probes of the compartments HERV-MalR and OPTI are designed according to the methodology presented above, whereas the probes of the compartment U133_HTA originate from two Affymetrix DNA chips, namely the "HG_U133_Plus2" chip (herein below "U133") and the chip marketed under the reference "HTA" respectively, and are therefore designed according to the methodology specific to the company Affymetrix. The compartment U133_HTA is therefore in reality two distinct probe sets originating from two Affymetrix chips targeting the same 1560 genes.

More particularly, for the design of the compartments HERV-MalR and OPTI, the length k of the k-hybrids is chosen to be equal to 5 and the number of areas M is chosen to be equal to 3. Only the probes for which the first affinity $\phi_1$ is above or equal to the threshold $S_1$ and for which the second affinities $\phi_2$ are strictly below the threshold $S_1$ are retained. The threshold $S_1$ is chosen to be equal to 4.4.

The compartment HERV_MalR of the chip V3, the largest, therefore constitutes an embodiment of the present invention. The other two compartments of the chip V3 (OPTI and U133_HTA) for their part allow for a comparison of the invention with probe sets designed according to the prior art methods. Each of these compartments therefore contains probes forming perfect hybrids with their target transcripts.

F.2.) Accuracy and Choice of the Affinity Prediction Model

Figure 12:
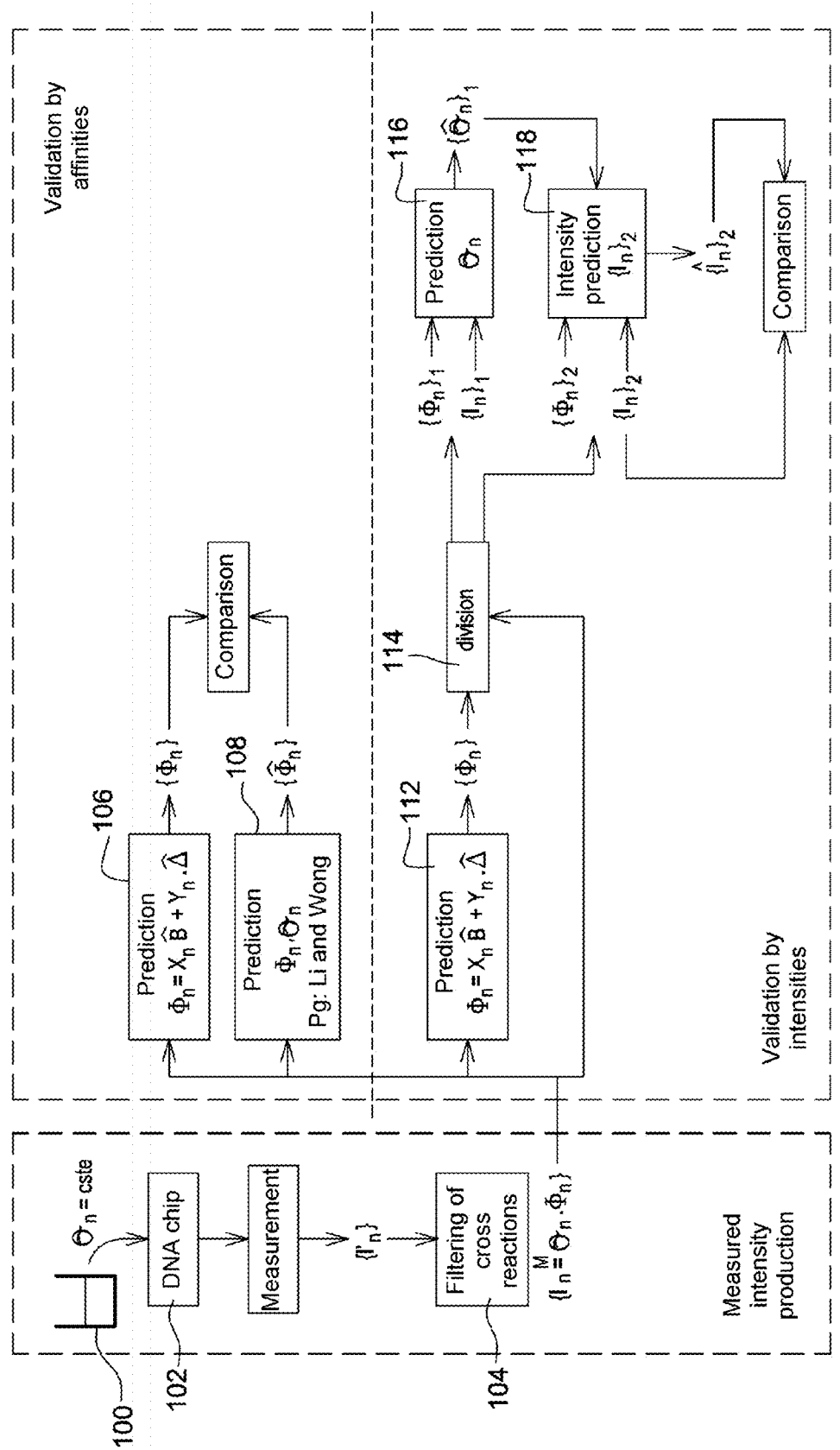
FIG. 12 is a diagram illustrating a protocol for validating probes for DNA chips designed according to the method of the invention.

The validation of an affinity prediction model according to the invention relies on the protocol illustrated in FIG. 12. A particular prediction model having been previously determined (therefore for a length k and a particular division M and previously learned corresponding matrices $\hat{B}$ and $\hat{\Delta}$), the validation protocol consists in comparing probe affinities predicted by the model with affinities "reconstructed" from measured intensities of the probes ("validation by affinities" branch, implemented by means of computer computations) and/or in comparing probe intensities predicted by the model to intensities measured for these probes ("validation by intensity" branch, implemented by means of computer computations). Whatever the branch selected, the protocol begins with the production of measured intensities ("production of measured intensities" branch, for the most part implemented by means of computer computations, except with respect to the production and the deposition of the solution deposited on the DNA chip).

The production of the measured intensities comprises a conventional step of production of a solution 100 from targeted transcripts known through a DNA chip 102 for which the probes are known, the deposition of the solution on the chip, washing and measurement of the intensities $\{I_n\}$ of the probes of the chip. Usually, the solution deposited on the DNA chip is homogenous such that the quantity of RNA of a transcript is identical for each of the wells of the chip. A filtering 104 of the intensities produced is then implemented to eliminate the intensities resulting from, or assumed as such, the cross-reactions or else correct the intensities as a function of the cross-reactions, in order to obtain probe intensities $\{I_n\}$ each corresponding to the hybrid formed by the probe with its target transcript, and therefore each modelable according to the relation $I_n = \theta_n \times \phi_n$, as is described above.

The "validation by affinities" branch, for its part, consists in:

predicting (in 106) the affinity $\phi_n$ of each of the probes associated with the intensities $\{I_n\}$ by using a model according to the invention $\phi_n = X_n \cdot \hat{B} + Y_n \cdot \hat{\Delta}$;

estimating (in 108) an affinity value $\hat{\phi}_n$ for each of the probes as a function of the intensities $\{I_n\}$. This computation is the one described in the article by Li and Wong "*Model-based analysis of oligonucleotide arrays: Expression index computation and outlier detection*", Proceedings of the National Academy of Sciences, 98(1): 31-36, 2001. This computation consists in particular in minimizing a cost function dependent on the differences $(I_n - \theta_n \times \phi_n)$ subject to the constraint $\Sigma \theta_n^2 = N$, the solution of this optimization problem being the affinity values $\hat{\phi}_n$ and predictions $\hat{\theta}_n$ of the quantities of RNA $\hat{\theta}_n$; and in comparing (in 110) the values $\phi_n$ and $\hat{\phi}_n$.

The "validation by intensities" branch, for its part, consists in:

predicting (in 112) the affinity $\phi_n$ of each of the probes associated with the intensities $\{I_n\}$ by using a model according to the invention $\phi_n = X_n \cdot \hat{B} + Y_n \cdot \hat{\Delta}$;

in dividing (in 114) the set of the intensities of the probes $\{I_n\}$ into two subsets $\{I_n\}_1$ and $\{I_n\}_2$ within each probe set, and, correspondingly, dividing the set of the predicted affinities $\{\phi_n\}$ into two subsets $\{\phi_n\}_1$ and $\{\phi_n\}_2$, in ⅔ and ⅓ proportions;

in predicting (in 116) the quantities of RNA $\phi_n$ as a function of the sets $\{I_n\}_1$ and $\{\phi_n\}_1$. In particular, this prediction consists of a linear regression between the set $\{I_n\}_1$ and the set $\{\phi_n \times \phi_n\}$ since the values of $\phi_n$ are already computed. A predicted value $\phi_n$ is thus obtained for each quantity of RNA $\phi_n$ poured into the wells of the DNA chip;

in predicting (in 118) the intensities of the subset $\{I_n\}_2$ according to the relation $\hat{I}_n = \hat{\theta}_n \times \phi_n$;

in comparing the intensities of the subset $\{I_n\}_2$ with their corresponding predictions $\{\hat{I}_n\}_2$.

Thus, the performance levels of the model are evaluated (i) at the affinities level, by correlating the affinities predicted by the model with the affinities estimated by the model of Li & Wong (2001) and (ii) at the intensity level, by correlating those predicted by the model with the observed intensities, these comparisons being performed probe-by-probe. In the first case, the correlations are computed within each probe set of the DNA chip because of the constraint $\Sigma\theta_n^2 = N$ imposed by the Li & Wong model. In other words, instead of correlating the affinities predicted by the model with those of Li & Wong globally over the set of the probes, the computation of the correlations is made probe-by-probe for each probe set.

The aim of the present example is to illustrate the accuracy of our affinity model according to the relation (3), that is to say its ability to finely predict the affinity of the probes. In this example, a validation by affinity is implemented.

Nine affinity prediction models according to the relation $\phi = \Sigma_{m=1}^{M} \Sigma_{p=1}^{P} x_{m,p} \cdot \hat{\beta}_{m,p} + \Sigma_{l=1}^{L} \cdot \hat{\delta}_l$ are tested. The two variables evaluated are the size of the k-hybrids (k varying from 3 to 5) and the inclusion of the spatial information according to three different scenarios: a probe is divided into 1, 3 and 25–k divisions (the last case is called "any position"). Each model is therefore associated with its own structure of the matrices X, Y, $\hat{B}$ and $\hat{\Delta}$ and with its own values of the matrices 11 and $\hat{\Delta}$. The learning of the models is performed in the way described in relation to the steps 82 to 88 of FIG. 10 (the steps 70-80 of FIG. 10 corresponding to the construction of the learning set of the first DNA chip) on the learning set of the first chip by using a conventional "10-fold cross-validation" approach in order to safeguard against the risks of overlearning during the learning of the parameters $\hat{B}, \hat{\Theta}, \hat{\Delta}$.

For the validation of the nine models according to the intensities, the probes used are those of the probe set "CD59" of the "genes" compartment of the chip V2, hybridized with six cellular rows (RWPE1 and five rows which derive therefrom). These cellular rows are homogeneous populations of cells originating from human samples (prostate epithelial cells) which have been transformed to augment their longevity. The protocols for hybridization (amplification, fragmentation, marking, hybridization on the chip) and for biocomputing processing of the measurements derived therefrom, are described in the document by Pérot et al. "*Microarray-based sketches of the HERV transcriptome landscape*". In particular, the raw intensities measured on the chips follow three biocomputing preprocessing steps usually followed in this type of analysis and detailed in the document "*Exploration, normalization, and summaries of high density oligonucleotide array probe level data, Biostatistics*" (Irizarry et al. 4(2): 249-64. April 2003). These three steps are the correction of the background noise, the inter-chip normalization, the summarizing which provides, for each probe set, an estimation of the quantity of hybridized RNA from the intensities of the probes which make up this probe set. This last step is performed by considering that the intensity of each probe is the sum of a target-probe affinity effect specific to the probe and of a RNA quantity effect common to all the probes of a subset. Each of these effects is estimated robustly using the so-called "median polish" method (see Irizarry et al. 2003).

Figure 13B:
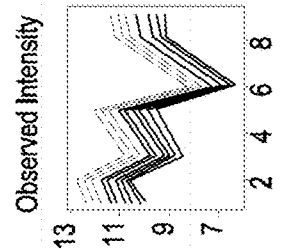
FIGS. 13A and 13B are graphs illustrating intensities predicted according to the invention and measured on a DNA chip.
Figure 13A:
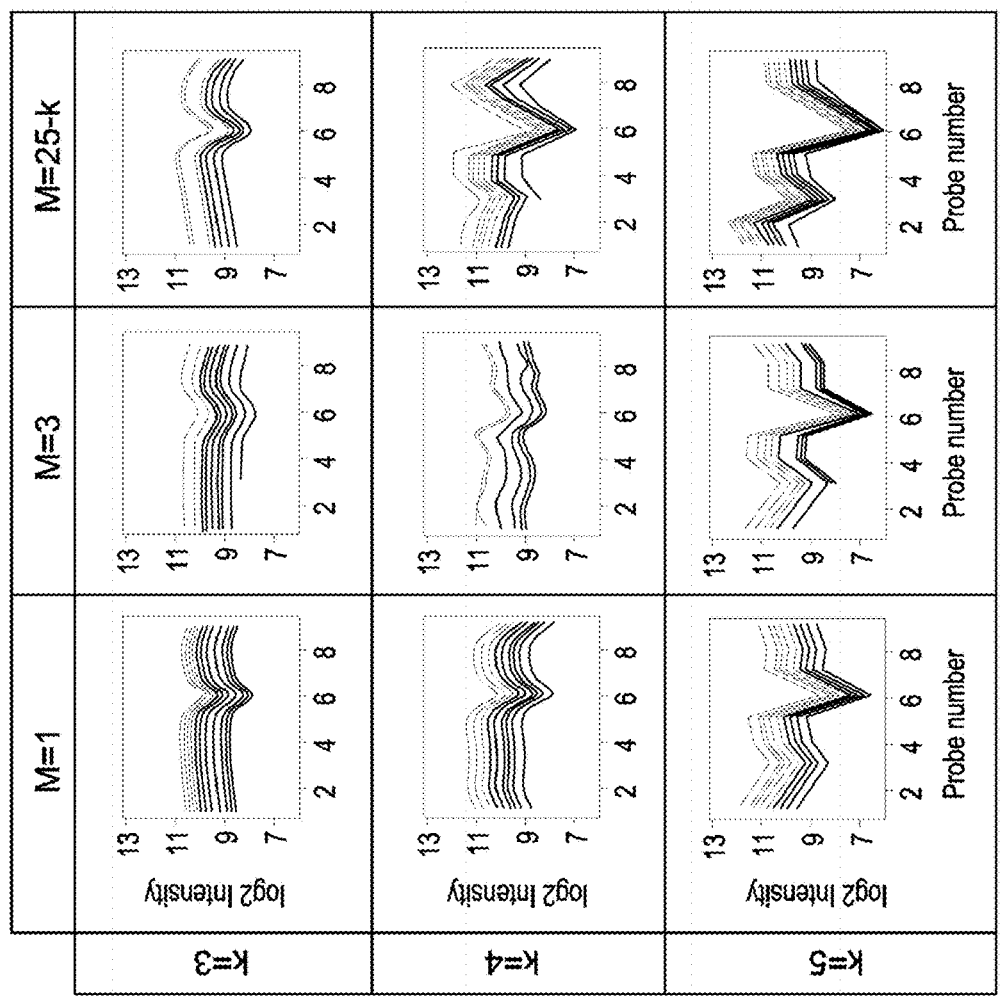

Sixteen tests were carried out, corresponding to a measurement on the probe sets CD59 of 16 chips V2 in order to demonstrate the accuracy of the models even faced with a strong variability of the measurements, notably because of the quantity of RNA deposited on the chips V2 which is not accurately controlled. The result of these tests is illustrated in FIGS. 13A and 13B. In these figures, the logarithm of the intensity is plotted as a function of the reference of the probes contained in the probe set CD59 (9 of them). Each plot also includes all of the 16 tests carried out, therefore 16 curves per plot. The intensities measured on the 16 probe sets CD59 are illustrated in FIG. 13B and the corresponding intensities predicted as a function of the nine affinity prediction models are illustrated in FIG. 13A. In the latter, the nine models are ranked by increasing complexity, from top to bottom by increasing k-hybrid and from left to right by increasing complexity of the spatial modelling. Two trends can clearly be seen in FIG. 13B: the capacity of these models to correctly model the affinity variations within the probe set increases with (i) the size of the k-hybrids and (ii) the complexity of the spatial information. It can be noted that the final model (5-hybrids 3-divisions) follows very accurately the intensities measured on chip. These performance levels are illustrated globally in the following example.

F.3.) Validity of the Affinity Prediction Model on Another Platform

The aim of the present example is to illustrate the performance levels of the affinity prediction model according to the invention on the 513 probe sets of the "genes" compartment of the chip V2 and to demonstrate the validity of the model for another DNA chip format, namely on the 3120 probe sets of the "U133_HTA" compartment of the chip V3. In effect, while the wells of the chip V2, of dimensions equal to those of the chip HERV-V2, measure 11 µm of side, those of the chip V3 measure only 5 µm.

To this end, a validation by affinities and a validation by intensity are implemented on an affinity prediction model characterized by a length of the k-hybrids equal to 5 (k=5) and by a division of the probes into 3 areas (M=3). As described previously, the inventors noted the good performance of this model, and even with a length k and a number M of areas that are reduced. The matrices $\hat{B}$ and $\hat{\Delta}$ of this model are learned on the learning set of the first DNA chip.

The biological samples used in this example are four different cellular rows of the applicant hybridized simultaneously in triplicate on 12 chips V2 and 12 chips V3 (4 rows×3 replicas=12 chips). The hybridization and biocomputing processing protocols used in this example are those described in the article by Pérot et al. "*Microarray-based sketches of the HERV transcriptome landscape.*".

FIGS. 14A and 14B illustrate the logarithm of the measured intensities $\{I_n\}_2$ as a function of the logarithm of the predicted intensities $\{\hat{I}_n\}_2$ respectively for the chip V2 and the chip V3. FIG. 14C illustrates the distribution of the determination coefficients (defined as the square of the determination coefficient, it represents the percentage variation of one variable explained by the other) of the chip V2 (genes compartment) and of the chip V3 (U133_HTA compartment).

FIGS. 14A and 14B show a good consistency between the measured intensities and the predicted intensities both on the chip V2 and on the chip V3, the correlation being slightly better on the chip V2 ($R^2=0.55$) than on the chip V3 ($R^2=0.45$). In FIG. 14C, it can be seen that the distribution of the determination coefficients reflect a good match between the affinities predicted by the model according to the invention and those estimated by the Li & Wong model. These results therefore demonstrate the capability of the model to correctly predict the affinity of the probes, and do so regardless of the format of the chip.

F.4.) Validity of the DNA Chip Design Method and Measurement Accuracy

A DNA chip can be seen as a measurement instrument whose aim is to maximize the biological variability and minimize the technical variability introduced by the tool. The technical variability, or error, is commonly decomposed as the resultant of a systematic error (or "bias") and a random error.

The present example studies the technical variability of a DNA chip obtained according to the design method according to the invention. The objective of the results presented in this example is to demonstrate that the probes designed with the probe selection methodology according to the invention, described in relation to FIGS. 1 to 8, give a good measurement accuracy, and consequently, return results consistent with those obtained with the DNA chips marketed by the company Affymetrix. The Affymetrix chips are chosen as comparison because of their recognized quality. This comparison is conducted on the chip V3 which comprises probe compartments designed according to the invention (the "HERV-MaLR" compartment and the "OPTI" compartment) and a compartment corresponding to an Affymetrix chip (the "U133_HTA" compartment).

The technical variability is studied using two criteria put forward by the "MicroArray Quality Check" (or "MAQC") consortium to judge the quality of a DNA chip: the repeatability (i.e. the variation of a measurement when it is repeated by an operator in the same conditions. This variation reflects the random error and the monotonic titration (a quantity close to the sensitivity of a DNA chip that makes it possible to measure the consistency between the intensities measured on a chip with hybridized RNA concentrations). These criteria are assessed hereinbelow.

The samples used for this assessment are those used by the MAQC consortium, as described in the document "*The MicroArray Quality Control (MAQC) project shows inter- and intraplatform reproducibility of gene expression measurements*", 24(9):1151-61. Nature Biotechnology, September 2006.

These samples originate from two samples of brain RNA (A) and of reference RNA known as "universal human reference RNA" (B) corresponding to a mixture of 10 cellular rows. These two samples are mixed in portions 3:1 (C=0.75×A+0.25×B) and 1:3 (D=0.25×A+0.75×B) to generate two additional samples C and D. Each of these samples is hybridized in triplicate on the chip V3. The hybridization and biocomputing processing protocols used in this example are described in the article by Pérot et al. ("*Microarray-based sketches of the HERV transcriptome landscape.*")

F.4.1.) Study of the Repeatability

In order to know the relevance of the comparison between a DNA chip designed according to the methodology according to the invention with an Affymetrix chip, a study is first of all conducted to ensure that no confusing effect skews this comparison.

The results of this study are represented in FIGS. 15A to 15G which illustrate the accuracy of the measurement and the identification of genes expressed differently for each of the compartments HERV_MalR (pink), U133_HTA (green) and OPTI (blue) of the chip V3.

FIGS. 15A and 15B respectively illustrate the distributions of the variables exhibiting a confusing effect, namely the intensities and the number of probes per probe sets. In FIG. 15A, the distribution for the compartment HERV_MalR is referenced by the letter "H", the distribution for the compartment U133_HTA is referenced by the letter "U" and the distribution for the compartment OPTI is referenced by the letter "O". In FIG. 15B, for each range represented on the X axis, the densities are, from left to right, those respectively of the HERV_MalR, U133_HTA and OPTI.

FIGS. 15C and 15D respectively illustrate the stratified variation coefficients per range of intensities at the probe level and at the probe set level. In these figures for each range represented on the X axis, the bars are, from left to right, those respectively of the HERV_MalR, U133_HTA and OPTI, and, additionally for FIG. 15D, that of a compartment "sampled_U133_HTA" described hereinbelow.

In reading these figures, it can be seen that the distributions of the intensities of the MAQC samples and those of the number of probes per probe set show that there is a great uniformity between the three compartments of the chip V3, making it possible to stratify the results by intensity and by probe set size. The measurement usually used to measure the repeatability is the coefficient of variation between the replicas, this computation is performed at the probe level (FIG. 15C) and at the probe set level (FIG. 15D). The comparison at the probe level shows that there is a strong effect of the intensity on the variation coefficient, but that, for a given intensity range, the three compartments exhibit identical performance levels. A same effect of the intensity is observed at the probe set level to which is added a probe set size effect: the variation coefficients are greater in HERV_MalR than U133_HTA, the first mostly containing three probes per probe set whereas the second exceeds seven probes per probe set in most of the cases. To ensure that the difference in repeatability between these two perimeters is closely linked to the size of the probe sets and not to the design of the probes, the probe sets U133_HTA are regenerated by using "X" probes drawn randomly from each probe set, X being a random variable distributed according to the size of the HERV_MalR probe sets. The newly formed probe sets ("sampled_U133_HTA") exhibit variation coefficients that are almost identical to those computed in the compartment HERV_MalR. That confirms that the repeatability of the probes studied is similar, and that regardless of the probe design method considered.

F.4.2) Monotonic Titration

FIGS. 15E and 15F represent the monotonic titrations at the probe and probe set level. Regarding FIG. 15F, the compartment "sampled_U133_HTA" is referenced by the letters "SU". The performance criterion used in this example reflects the consistency between the RNA concentration hybridized on the chip and the observed signal. By using two dilutions (C and D) with known levels, the ranks of the intensities of C and D have to be able to be deduced from the relative expression of the starting samples (A and B).

Thus, if, for a probe set i, we have the relation $A\_i > B\_i$ then $A\_i > C\_i > D\_i > B\_i$. When the probe set percentage observing this hierarchy is represented as a function of their ratio AB and B/A, the expected form of a graph representing the monotonic titration, as represented in FIGS. 15E and 15F, is a "V" with horizontal asymptotes at the ends of the branches. Consequently, a probe design method is optimal if the percentage of titration reaches the 100% threshold for low ratios $A\_i/B\_i$. In other words, the closer together the branches of the "V", the better the associated method.

In the same way as in the repeatability study, the three compartments are compared at the probe and probe set levels, by correcting the effect linked to the size of the probe sets in the second case. At the probe level, the compartment OPTI gives better performance levels than the other two compartments (FIG. 15E). At the probe set level, the compartments OPTI and U133_HTA exhibit probe set percentages observing A_i>C_i>D_i>B_i that are almost identical and slightly higher than those computed in the compartments HERV_MalR and sampled_U133_HTA (FIG. 15F). Thus, for the set of the 1560 genes studied, the DNA chip design method according to the invention gives results slightly better than Affymetrix at the probe level and equivalent results at the probe set level, and does so despite the smaller probe sets.

F.4.3) Differently Expressed Genes

Figure 15G:
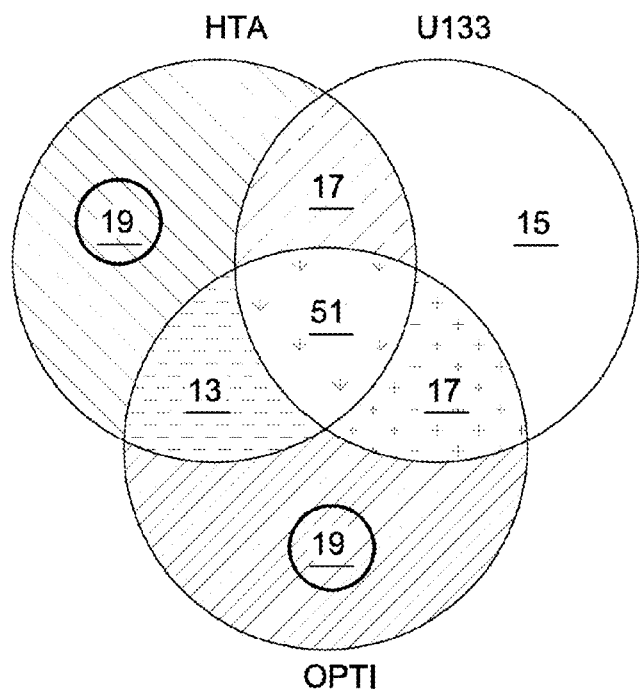

Finally, FIG. 15G presents the consistency between the compartments OPTI, U133 and HTA in the identification of genes expressed differently between the samples A and B. This type of approach is widely used in the studies using DNA chips, in effect the latter are rarely used to study the absolute expression of transcripts in a tissue and a given condition, but rather in the context of studies aiming to identify transcripts whose level of expression varies between two or more conditions. In FIG. 15G, the Venn diagram represents the intersection of the 100 genes having the greatest expression differential in the compartments OPTI, U133 and HTA.

The aim of this example is to show that the 100 genes having the strongest expression differential between the two samples A and B of the MAQC are comparable in the compartments OPTI and U133_HTA (U133 and HTA) of the chip V3. The differently expressed genes are identified using the SAM method described in the document "*Significance analysis of microarrays applied to the ionizing radiation response.*", Tusher V G, Tibshirani R, Chu G. Proceedings of the National Academy of Sciences of the USA. April 2001 24; 98(9):5116-21, then for each of the three compartments of the chip V3, the 100 genes with the lowest p-value are retained. The intersections between these three compartments are represented in the Venn diagram of FIG. 15G, where it can be seen that the number of common genes between the OPTI and the Affymetrix compartments (U133 and HTA) is very close to the number of genes shared between U133 and HTA. In other words, the consistency of the results between OPTI and U133/HTA is of the same order as that which exists between U133 and HTA, both compartments designed by Affymetrix. The percentage overlap (~65%) is also in the high average of the values found by the MAQC consortium in their interplatform comparison. These results thus demonstrate that the identification of differently expressed genes with the OPTI probes is consistent with the Affymetrix probes.

F.5) Specificity of the Measurements

The aim of the present example is to demonstrate that the hybridization model according to the invention serves not only to compute the target-probe affinity, but that it can also be used to measure the specificity of the probes. The objective of the compartment HERV-MalR of the chip V3 is to specifically characterize the level of expression of the HERVs, organized in some forty multicopy families in the human genome. The repeated nature of these elements renders the individual measurement thereof difficult.

To check the specificity of the probes, a specificity score Spec=$\phi_1$-max($\phi_2$) is computed. In other words, for a given probe, this score measures the affinity difference between the specific hybrid and the stablest non-specific hybrid, i.e. the one which exhibits the greatest risk of cross-reaction. To test the validity of this specificity score, two types of experiment can be implemented:

for a given probe, create "spike-ins" RNA (i.e. RNAs artificially synthesized in a laboratory) complementing mismatches and check that the decrease in intensities is linked to the increase in the specificity score, the latter being computed as the affinity difference between the specific target, absent from the reaction mixture, and the hybridized non-specific target. This type of approach offers the advantage of accurately knowing which RNAs are present in the reaction mixture;

hybridizing a same biological sample on the chips V2 and V3 and correlating the intensities of the HERV/MarR loci common to both chips. More specifically, the specificity score as described above is computed for all of the probes, then, in calculating the correlation, only the probe sets for which the probes exceed a given specificity threshold are taken into account. If the specificity score is valid, the correlation between the intensities of V2 and V3 should increase with the specificity level. This approach which is more global than the preceding one is the one chosen in this example.

The biological samples used in this example originate from the same four cellular rows as those presented in the example F. The hybridization and biocomputing processing protocols used in this example are described in the article by Pérot et al. ("*Microarray-based sketches of the HERV transcriptome landscape*") and comprise the usual steps of amplification, of fragmentation, of marking, of hybridization on the chip, followed by steps of background correction, of normalization and of summarization.

Figure 16A:
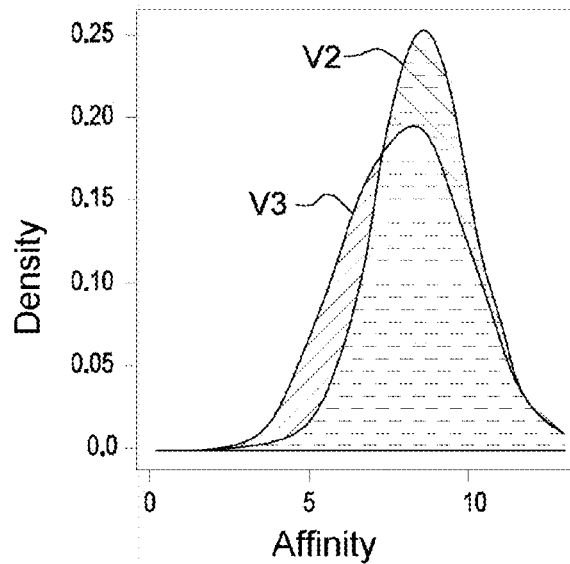
FIGS. 16A to 16C are graphs illustrating the specificity of the probes of a DNA chip designed according to the method of the invention.
Figure 16B:
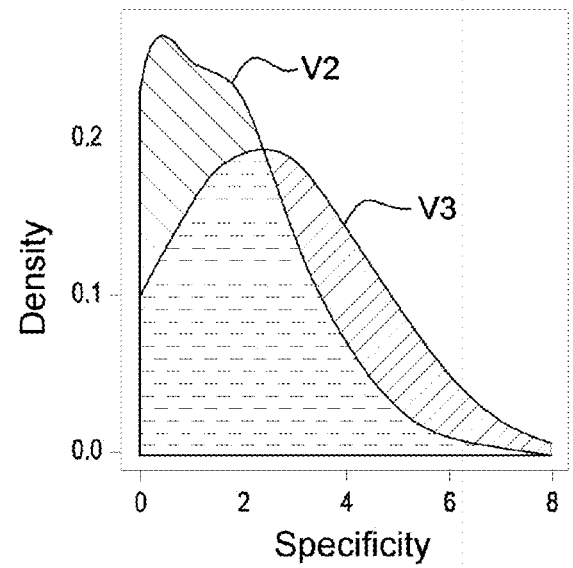
Figure 16C:
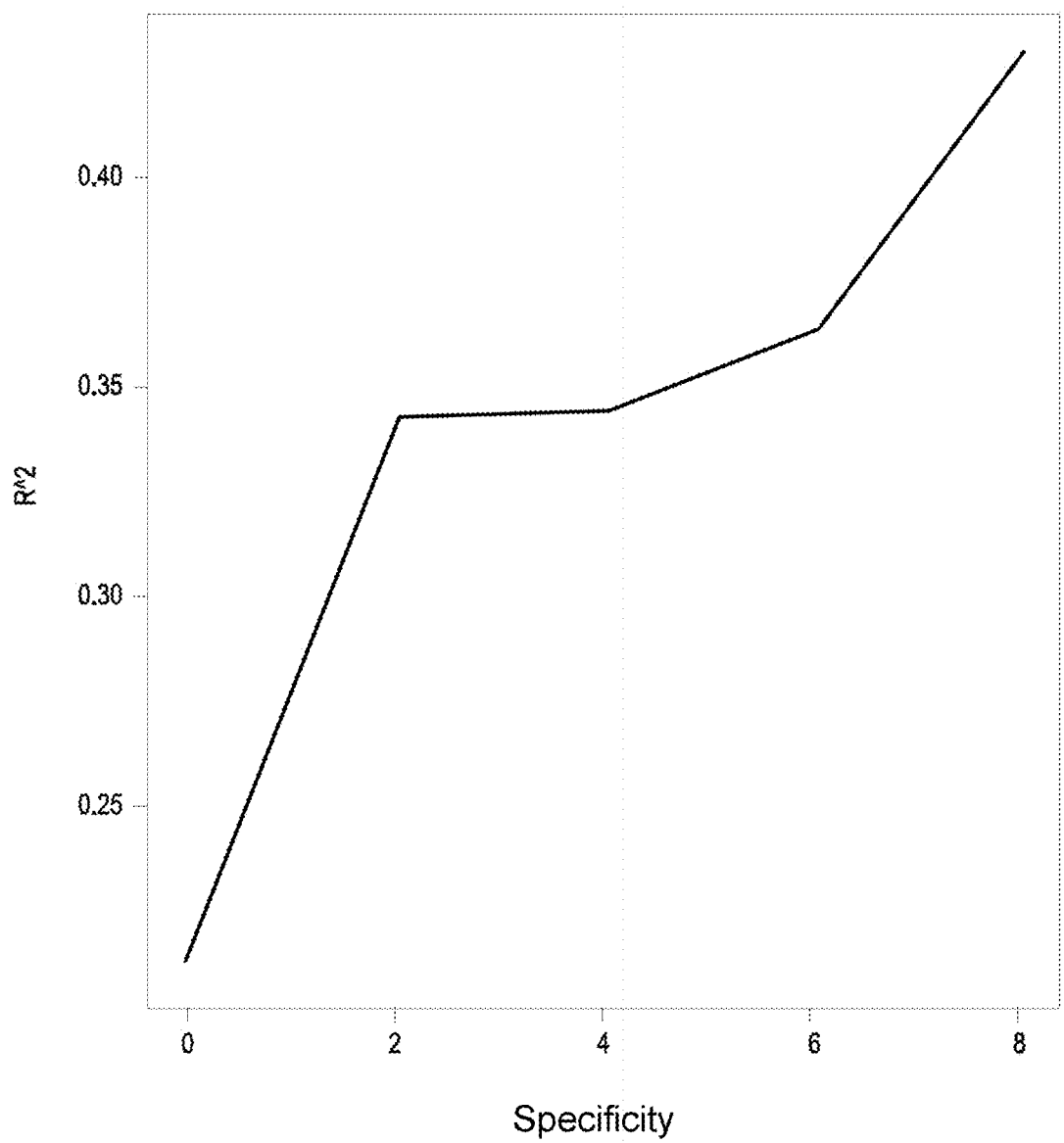

FIGS. 16A to 16C illustrate comparisons of scores of affinity and of specificities of the probes belonging to the elements common to the chips V2 and V3. FIGS. 16A and 16B respectively illustrate the distributions by percentage of the affinity and specificity scores and FIG. 16C illustrates the determination coefficient between the intensities measured by the chips V2 and V3 as a function of the specificity score on the same elements common to these chips.

In FIGS. 16A and 16B, the comparison of the affinity score, that is to say the first affinity $\phi_1$ and of the specificity score Spec of the probes belonging to the common elements of the chips V2 and V3, shows that the probes V2 are on average more affine but less specific than those of the chip V3. It can then be seen, notably in FIG. 16C, that the measurements performed by the chips V2 and V3 on the same elements exhibit a correlation that increases as the specificity of the probes increases. This means that the specificity score makes it possible to discern the not very specific probes which cross-hybridize with non-specific transcripts of the specific probes which hybridize with the same transcripts on both chips and consequently gives higher correlations. This example demonstrates that the affinity model serves not only to design optimal probes but also to check the specificity of the probes.

G) Extension of the Teaching of the Embodiment Detailed k-hybrids have been described whose length is strictly equal to k. Obviously, the invention also covers a subdivision of the hybrids into k-hybrids whose length is less than or equal to k, that is to say into hybrid portions of length strictly equal to k, into hybrid portions strictly equal to k−1, etc. The mathematical framework described above content to be applied, the design matrices X and Y and the contribution vectors $\hat{B}$ and $\hat{\Delta}$ and being simply increased in size to take account of the additional configurations of k-hybrids.

A subdivision of the hybrids into areas of equal length has been described. The invention applies equally to areas of different length, which makes it possible to more accurately take account of the influence of each area.

A DNA chip probe selection method has been described based on a particular inventive modeling of affinity. The selection method according to the invention can however be based on other types of affinity modeling, the final threshold-based selection rules remaining identical.

Similarly, particular mathematical equations have been described. As is known per se, there can be, for each equation, several possible equivalent mathematical expressions, these different expressions lying also within the scope of the invention.

The invention claimed is:

1. A method for estimating an affinity $\phi$ of a first DNA strand, or "probe", to be hybridized with a second DNA strand, or "target", to form a hybrid of a length $L_{bp}$, the method comprising:

in each division of a set of M divisions of the hybrid, counting a number of times in which each hybrid of a set of P DNA strand hybrids is present in the division, the hybrids being of a length k less than the length $L_{bp}$, or "k-hybrids";

for each pair of mismatches of a set of L pairs of mismatches in the hybrid of the length $L_{bp}$, determining whether the pair of mismatches is present in the hybrid; and calculating the affinity $\phi$ according to the relation:

$$\phi = \sum_{m=1}^{M} \sum_{p=1}^{P} x_{m,p} \cdot \hat{\beta}_{m,p} + \alpha$$

in which:

$\forall (m,p) \in [1,M] \times [1,P]$, $\hat{\beta}_{m,p}$ is a predetermined scalar quantifying the contribution to the affinity $\phi$ of a $p^{th}$ k-hybrid of the set of P k-hybrids when this $p^{th}$ k-hybrid is present in a $m^{th}$ area of the division;

$x_{m,p}$ is a number of times in which this $p^{th}$ k-hybrid is counted for the hybrid in the $m^{th}$ area of the division; and $\alpha$ is a real term.

2. The method as claimed in claim 1, in which $$\alpha = \sum_{l=1}^{L} y_l \cdot \hat{\delta}_l + \pi$$

in which $\forall l \in [1,L]$, $\hat{\delta}_l$ is a predetermined scalar quantifying the contribution to the affinity $\phi$ of a $l^{th}$ pair of mismatches; $y_l=1$ if the $l^{th}$ pair of mismatches is present in the hybrid and $y_l=0$ otherwise; and $\pi$ is a predetermined real number.

3. The method as claimed in claim 2, further comprising:

for each pair of a set of N calibration pairs each comprising first and second DNA strands capable of together forming the hybrid of length $L_{bp}$, bringing together a quantity of the first DNA strand of the pair with a quantity of the second DNA strand of the pair;

measuring an intensity $I_n$ representative of a quantity of DNA strand hybrids formed following this bringing together, the hybrids of the calibration pairs comprising each k-hybrid of the set of P k-hybrids at least once; and calculating a vector $\hat{B} \in \mathbb{R}^{P \cdot M}$, a vector $\hat{\Theta} \in \mathbb{R}^{N}$ and a vector $\hat{\Delta} \in \mathbb{R}^{L}$ minimizing a distance D between a vector $I=(I_1 \ldots I_n \ldots I_N)^T \in \mathbb{R}^{N}$ of the measured intensities and a vector $M=(M_1 \ldots M_n \ldots M_N)^T \in \mathbb{R}^{N}$ representing a prediction of the vector I of the measured intensities, the calculation being performed by solving an optimization problem according to the relations:

$$(\hat{B}, \hat{\Theta}, \hat{\Delta}) = \arg \min_{B,\Theta,\Delta} D(I, M)$$

and $$\forall n \in [1, N], M_n = \theta_n \cdot (X_n \cdot B + Y_n \cdot \Delta)$$

in which:

$\Theta = (\theta_1 \ldots \theta_n \ldots \theta_N)^T$ is a vector of $\mathbb{R}^N$, in which $\forall n \in [1,N]$, $\theta_n$ is a scalar coding a quantity of the first and/or the second DNA strands brought together for a $n^{th}$ calibration pair;

$\forall n \in [1,N]$, $X_n = (x_{n,1} \ldots x_{n,m} \ldots x_{n,M})$ is a row matrix of predetermined design of $\mathbb{R}^{P \cdot M}$, in which $\forall m \in [1,M]$, $X_{n,m} = (x_{n,m,1} \ldots x_{n,m,p} \ldots x_{n,m,P})$ is a row matrix of $\mathbb{R}^P$ and $\forall p \in [1,P]$, $x_{n,m,p}$ is a number of times in which the $p^{th}$ k-hybrid is present in the $m^{th}$ area of the division for the hybrid formed by the first and second DNA strands of the $n^{th}$ calibration pair;

$B = (B_1 \ldots B_m \ldots B_M)^T$ is a vector of $\mathbb{R}^{P \cdot M}$, in which $\forall m \in [1,M]$, $B_m = (\beta_{m,1} \ldots \beta_{m,p} \ldots \beta_{m,P})^T$ is a vector of $\mathbb{R}^P$, with $\forall p \in [1,P]$, $\beta_{m,p}$ is a scalar quantifying the contribution to the affinity of the hybrid of the length $L_{bp}$ of the $p^{th}$ k-hybrid of the set of P k-hybrids when this $p^{th}$ k-hybrid is present in the $m^{th}$ area of the division;

$\forall n \in [1,N]$, $Y_n = (y_{n,1} \ldots y_{n,l} \ldots y_{n,L})$ is a row matrix of predetermined design of $\mathbb{R}^L$, in which $\forall l \in [1,L]$, $y_{n,l} = 1$ if the $l^{th}$ pair of mismatches is present in the hybrid formed by the first and second DNA strands of the $n^{th}$ calibration pair; and $\Delta = (\delta_1 \ldots \delta_l \ldots \delta_L)^T$ is a vector of $\mathbb{R}^L$, in which $\forall l \in [1,L]$, $\delta_l$ is a scalar quantifying the contribution to the affinity of the hybrid of the length $L_{bp}$ of the $l^{th}$ pair of mismatches.

4. The method as claimed in claim 1, wherein the k-hybrids have a length k of between 2 and 7 and the number M of areas of the division is between 2 and 25-k.

5. The method as claimed in claim 4, wherein the number M of areas is between 3 and 15.

6. The method as claimed in claim 4, wherein the k-hybrids have a length k of between 3 and 5.

7. The method as claimed in claim 3, wherein the solving of the optimization problem is subject to the additional constraint according to the relation:

$$\sum_{i=1}^{I} \theta_i^2 = \alpha$$

in which I is a number of different RNAs and $\alpha$ is a predetermined positive scalar.

8. The method as claimed in claim 3, wherein the optimization problem is solved iteratively:

by setting, on the iteration i, the vectors B, $\Delta$ to their values calculated on the preceding iteration i−1 and by solving the optimization problem according to the relations:

$$(\hat{\Theta}(i)) = \arg\min_{\Theta(i)} D(I, M(i))$$

and $$\forall n \in [1, N], M_n(i) = \theta_n(i) \cdot (X_n \cdot B(i-1) + Y_n \cdot \Delta(i-1))$$

by setting, on the iteration i+1, the vector $\Theta$ to its value calculated on the iteration i, and by solving the optimization problem according to the relations:

$$(\hat{B}(i+1), \hat{\Delta}(i+1)) = \arg\min_{B(i+1), \Delta(i+1)} D(I, M(i+1))$$

and $$\forall n \in [1, N], M_n(i+1) = \theta_n(i) \cdot (X_n \cdot B(i+1) + Y_n \cdot \Delta(i+1)).$$

9. The method as claimed in claim 8, wherein the first iteration is performed by setting $\forall n \in [1,N]$, $X_n \cdot B(1) + Y_n \cdot \Delta(1) = 1$.

10. A method for estimating contributions $\hat{\beta}_{m,p}$ of hybrids of a set of P DNA strand hybrids of a length k, or "k-hybrids", to an affinity of a DNA strand hybrid of a length $L_{bp}$, comprising:

for each pair of a set of N calibration pairs each comprising a first and second DNA strands capable of together forming the hybrid of the length $L_{bp}$, bringing together a quantity of the first DNA strand of the pair with a quantity of the second DNA strand of the pair;

measuring an intensity $I_n$ representative of a quantity of DNA strand hybrids formed following this bringing together, the hybrids of the calibration pairs comprising each k-hybrid of the set of P k-hybrids at least once; and calculating a vector $\hat{B} \in \mathbb{R}^{P \cdot M}$, a vector $\hat{\Theta} \in \mathbb{R}^N$ and a vector $\hat{\Delta} \in \mathbb{R}^L$ minimizing a distance D between a vector $I = (I_1 \ldots I_n \ldots I_N)^T \in \mathbb{R}^N$ of the measured intensities and a vector $M = (M_1 \ldots M_n \ldots M_N)^T \in \mathbb{R}^N$ representing a prediction of the vector I of the measured intensities, the calculation being performed by solving an optimization problem according to the relations:

$$(\hat{B}, \hat{\Theta}, \hat{\Delta}) = \arg\min_{B,\Theta,\Delta} D(I, M)$$

and $$\forall n \in [1, N], M_n = \theta_n \cdot (X_n \cdot B + Y_n \cdot \Delta)$$

in which:

$\Theta = (\theta_1 \ldots \theta_n \ldots \theta_N)^T$ is a vector of $\mathbb{R}^N$, in which $\forall n \in [1,N]$, $\theta_n$ is a scalar coding a quantity of the first and/or the second DNA strands brought together for a $n^{th}$ calibration pair;

$\forall n \in [1,N]$, $X_n = (X_{n,1} \ldots X_{n,m} \ldots X_{n,M})$ is a row matrix of predetermined design of $\mathbb{R}^{P \cdot M}$, in which $\forall m \in [1,M]$, $X_{n,m} = (X_{n,m,1} \ldots X_{n,m,p} \ldots x_{n,m,P})$ is a row matrix of $\mathbb{R}^P$ and $\forall p \in [1,P]$, $x_{n,m,p}$ is a number of times in which the $p^{th}$ k-hybrid is present in the $m^{th}$ area of the division for the hybrid formed by the first and second DNA strands of the $n^{th}$ calibration pair;

$B = (B_1 \ldots B_m \ldots B_M)^T$ is a vector of $\mathbb{R}^{P \cdot M}$, in which $\forall m \in [1,M]$, $B_m = (\beta_{m,1} \ldots \beta_{m,p} \ldots \beta_{m,P})^T$ is a vector of $\mathbb{R}^P$, with $\forall p \in [1,P]$, $\beta_{m,p}$ is a scalar quantifying the contribution to the affinity of the hybrid of the length $L_{bp}$ of the $p^{th}$ k-hybrid of the set of P k-hybrids when this $p^{th}$ k-hybrid is present in the $m^{th}$ area of the division;

$\forall n \in [1,N]$, $Y_n = (y_{n,1} \ldots y_{n,l} \ldots y_{n,L})$ is a row matrix of predetermined design of $\mathbb{R}^L$, in which $\forall l \in [1,L]$, $y_{n,l} = 1$ if the $l^{th}$ pair of mismatches is present in the hybrid formed by the first and second DNA strands of the $n^{th}$ calibration pair; and $\Delta = (\delta_1 \ldots \delta_l \ldots \delta_L)^T$ is a vector of $\mathbb{R}^L$, in which $\forall l \in [1,L]$, $\delta_l$ is a scalar quantifying the contribution to the affinity of a hybrid of length $L_{bp}$ of the $l^{th}$ pair of mismatches.

11. A non-transitory computer-readable medium comprising instructions that perform the method as claimed in claim 1 when executed on a processor.

12. A method for fabricating a DNA chip comprising copies of a DNA strand, or probe, capable of forming a hybrid of a length $L_{bp}$ with a target strand of nucleic acid of a length greater than the length $L_{bp}$ without mismatch, the method consisting in comprising:

identifying a set of portions of the length $L_{bp}$ on the target DNA strand;

for each identified portion of the target DNA strand, or "candidate target":

determining a complementary DNA strand, or "candidate probe", and calculating a first affinity φ of the candidate probe with the candidate target by implementing the method as claimed in claim 1;

calculating a second affinity φ of the candidate probe with each element of a set of nucleic strands not comprising the candidate target by implementing the method as claimed in claim 1; and selecting, from the determined candidate probes, at least one probe, such that the first affinity φ calculated for the selected candidate probe is above a predetermined first threshold $S_1$ and each of the second affinities φ calculated for the selected candidate probe is below a second threshold $S_2$ strictly lower than the first threshold $S_1$; and fabricating the DNA chip with each selected candidate probe.

13. The method for fabricating a DNA chip as claimed in claim 12, wherein the at least one probe is selected for which at most N calculated affinities are above the first threshold $S_1$ and for which the second affinities φ are below the second threshold $S_2$ strictly lower than the first threshold $S_1$.

* * * * *